United States Patent
Shadduck et al.

(10) Patent No.: US 9,549,754 B2
(45) Date of Patent: Jan. 24, 2017

(54) TISSUE EXTRACTION DEVICES AND METHODS

(71) Applicant: IOGYN, INC., Cupertino, CA (US)

(72) Inventors: John H. Shadduck, Menlo Park, CA (US); Aaron Germain, San Jose, CA (US); Kyle Klein, San Jose, CA (US); Michael D. Walker, San Francisco, CA (US); Csaba Truckai, Saratoga, CA (US)

(73) Assignee: IOGYN, INC., Cupertino, CA (US)

( * ) Notice: Subject to any disclaimer, the term of this patent is extended or adjusted under 35 U.S.C. 154(b) by 260 days.

(21) Appl. No.: 14/249,032

(22) Filed: Apr. 9, 2014

(65) Prior Publication Data

US 2014/0221997 A1 Aug. 7, 2014

Related U.S. Application Data

(60) Continuation of application No. 13/910,873, filed on Jun. 5, 2013, now Pat. No. 8,728,066, which is a
(Continued)

(51) Int. Cl.
*A61B 18/00* (2006.01)
*A61B 17/3205* (2006.01)
(Continued)

(52) U.S. Cl.
CPC ..... *A61B 17/3205* (2013.01); *A61B 17/32002* (2013.01); *A61B 18/00* (2013.01);
(Continued)

(58) Field of Classification Search
CPC .................. A61B 2018/1467; A61B 17/32053; A61B 2017/320028; A61B 17/320016; A61B 17/320783
See application file for complete search history.

(56) References Cited

U.S. PATENT DOCUMENTS 4,650,462 A    3/1987  DeSatnick et al.
4,735,603 A    4/1988  Goodson et al.
(Continued)

FOREIGN PATENT DOCUMENTS

EP    2100567 A1    9/2009
GB    2327351 A     1/1999
(Continued)

OTHER PUBLICATIONS

AAGL Practice Report: Practice Guidelines for the Management of Hysteroscopic Distending Media: (Replaces Hysteroscopic Fluid Monitoring Guidelines. J Am Assoc Gynecol Laparosc. 2000;7: 167-168) J Minim Invasive Gynecol. Mar.-Apr. 2013;20:137-48. doi: 10.1016/j.jmig.2012.12.002.
(Continued)

*Primary Examiner* — Jocelyn D Ram
(74) *Attorney, Agent, or Firm* — Seager, Tufte & Wickhem, LLP

(57) ABSTRACT

Tissue may be cut and extracted from an interior location in a patient's body using a probe or tool which both effects cutting and causes vaporization of a liquid or other fluid to propel the cut tissue through an extraction lumen of the cutting device. The cutting may be achieved using an electrosurgical electrode assembly, including a first electrode on a cutting member and a second electrode within a cutting probe or tool. Thus, over a first cutting portion, radio frequency current may help cut the tissue and over a second or over transition region, the RF current may initiate vaporization of the fluid or other liquid to propel the tissue from the cutting device.

20 Claims, 26 Drawing Sheets

Related U.S. Application Data division of application No. 13/277,913, filed on Oct. 20, 2011, now Pat. No. 8,512,326.

(60) Provisional application No. 61/501,106, filed on Jun. 24, 2011, provisional application No. 61/531,985, filed on Sep. 7, 2011.

(51) Int. Cl.
  *A61B 18/18* (2006.01)
  *A61B 18/14* (2006.01)
  *A61B 17/32* (2006.01)
  *A61B 18/04* (2006.01)

(52) U.S. Cl.
  CPC .......... *A61B 18/1482* (2013.01); *A61B 18/18* (2013.01); *A61B 2017/320028* (2013.01); *A61B 2018/00196* (2013.01); *A61B 2018/00202* (2013.01); *A61B 2018/00589* (2013.01); *A61B 2018/00601* (2013.01); *A61B 2018/00625* (2013.01); *A61B 2018/048* (2013.01); *A61B 2218/007* (2013.01)

(56) References Cited

U.S. PATENT DOCUMENTS

| | | | |
|---|---|---|---|
| 5,098,375 A | 3/1992 | Baier | |
| 5,106,364 A | 4/1992 | Hayafuji et al. | |
| 5,277,696 A | 1/1994 | Hagen et al. | |
| 5,382,229 A | 1/1995 | Grabenkort et al. | |
| 5,437,629 A | 8/1995 | Goldrath | |
| 5,643,203 A | 7/1997 | Beiser et al. | |
| 5,669,921 A | 9/1997 | Berman et al. | |
| 5,730,752 A | 3/1998 | Alden et al. | |
| 5,810,858 A | 9/1998 | Berman et al. | |
| 5,823,990 A | 10/1998 | Henley et al. | |
| 5,830,180 A | 11/1998 | Chandler et al. | |
| 5,853,392 A | 12/1998 | Dennis | |
| 5,906,615 A | 5/1999 | Thompson | |
| 5,925,050 A | 7/1999 | Howard, III | |
| 6,032,673 A | 3/2000 | Savage et al. | |
| 6,109,268 A | 8/2000 | Thapliyal et al. | |
| RE36,914 E | 10/2000 | Carlsen et al. | |
| 6,206,014 B1 | 3/2001 | Cameron, III et al. | |
| 6,245,084 B1 | 6/2001 | Mark et al. | |
| 6,358,263 B2 | 3/2002 | Mark et al. | |
| 6,629,986 B1* | 10/2003 | Ross | A61B 17/32002 604/22 |
| 7,029,451 B2 | 4/2006 | Anderson et al. | |
| 7,070,604 B1 | 7/2006 | Garito et al. | |
| 7,204,821 B1 | 4/2007 | Clare et al. | |
| 7,226,459 B2 | 6/2007 | Cesarini et al. | |
| 7,384,417 B2 | 6/2008 | Cucin | |
| 7,510,535 B2* | 3/2009 | Hibner | A61B 10/0275 600/566 |
| 7,549,987 B2 | 6/2009 | Shadduck | |
| 7,674,259 B2 | 3/2010 | Shadduck | |
| 7,892,229 B2 | 2/2011 | Shadduck et al. | |
| 8,313,485 B2 | 11/2012 | Shadduck | |
| 8,512,326 B2 | 8/2013 | Shadduck et al. | |
| 8,728,066 B2 | 5/2014 | Shadduck et al. | |
| 2002/0010463 A1 | 1/2002 | Mulier et al. | |
| 2002/0072745 A1 | 6/2002 | Truckai et al. | |
| 2003/0009164 A1* | 1/2003 | Woloszko | A61B 18/1445 606/41 |
| 2003/0060862 A1* | 3/2003 | Goble | A61B 17/32002 607/96 |
| 2003/0208200 A1* | 11/2003 | Palanker | A61B 18/042 606/45 |
| 2004/0049217 A1* | 3/2004 | Ross | A61B 17/32002 606/171 |
| 2004/0092980 A1 | 5/2004 | Cesarini et al. | |
| 2004/0102770 A1 | 5/2004 | Goble | |
| 2004/0167427 A1* | 8/2004 | Quick | A61B 10/0275 600/564 |
| 2004/0167428 A1 | 8/2004 | Quick et al. | |
| 2004/0199226 A1* | 10/2004 | Shadduck | A61B 18/04 607/96 |
| 2004/0267255 A1 | 12/2004 | Auge, II et al. | |
| 2005/0096649 A1 | 5/2005 | Adams | |
| 2005/0236329 A1 | 10/2005 | Brotherton et al. | |
| 2006/0047185 A1 | 3/2006 | Shener et al. | |
| 2006/0135955 A1 | 6/2006 | Shadduck | |
| 2006/0224154 A1 | 10/2006 | Shadduck et al. | |
| 2007/0016182 A1 | 1/2007 | Lipson et al. | |
| 2007/0021713 A1 | 1/2007 | Kumar et al. | |
| 2007/0036768 A1 | 2/2007 | Fraser et al. | |
| 2007/0088275 A1 | 4/2007 | Stearns et al. | |
| 2007/0244353 A1 | 10/2007 | Larsen | |
| 2008/0039832 A1* | 2/2008 | Palanker | A61B 18/042 606/39 |
| 2008/0065060 A1 | 3/2008 | Ein-Gal | |
| 2008/0091061 A1 | 4/2008 | Kumar et al. | |
| 2008/0091071 A1 | 4/2008 | Kumar et al. | |
| 2008/0103504 A1* | 5/2008 | Schmitz | A61B 17/320016 606/79 |
| 2008/0287893 A1 | 11/2008 | Ineson | |
| 2009/0082715 A1 | 3/2009 | Charles | |
| 2009/0137943 A1 | 5/2009 | Stearns et al. | |
| 2009/0270898 A1 | 10/2009 | Chin et al. | |
| 2009/0312753 A1 | 12/2009 | Shadduck | |
| 2010/0100091 A1 | 4/2010 | Truckai | |
| 2010/0145325 A1* | 6/2010 | Hoey | A61B 18/04 606/27 |
| 2010/0152533 A1 | 6/2010 | Mark | |
| 2010/0152724 A1* | 6/2010 | Marion | A61B 5/01 606/33 |
| 2011/0224486 A1 | 9/2011 | Nguyen et al. | |
| 2011/0264090 A1 | 10/2011 | Shadduck et al. | |
| 2011/0306968 A1 | 12/2011 | Beckman et al. | |
| 2012/0053583 A1 | 3/2012 | Palanker et al. | |
| 2012/0271300 A9 | 10/2012 | Shadduck et al. | |
| 2012/0330292 A1 | 12/2012 | Shadduck et al. | |
| 2013/0046304 A1 | 2/2013 | Germain et al. | |
| 2013/0079702 A1 | 3/2013 | Klein et al. | |
| 2013/0103021 A1 | 4/2013 | Germain et al. | |
| 2013/0172805 A1 | 7/2013 | Truckai et al. | |
| 2013/0172870 A1 | 7/2013 | Germain et al. | |
| 2013/0231652 A1 | 9/2013 | Germain et al. | |
| 2013/0296847 A1 | 11/2013 | Germain et al. | |

FOREIGN PATENT DOCUMENTS

| | | |
|---|---|---|
| WO | 2010096139 A2 | 8/2010 |
| WO | 2010096139 A3 | 12/2011 |

OTHER PUBLICATIONS

Liu, et al. Clinical application of hysteriscopic electroresection in 775 cases. Di YHi Jun Yi Da Xue Xue Bao. Apr. 2004;24(4):467-9. (in Chinese with English abstract).

Phillips, et al. The Effect of Dilute Vasopressin Solution on Blood Loss During Operative Hysteroscopy. J Am Assoc Gynecol Laparosc. Aug. 1996;3(4, Supplement):S38.

\* cited by examiner

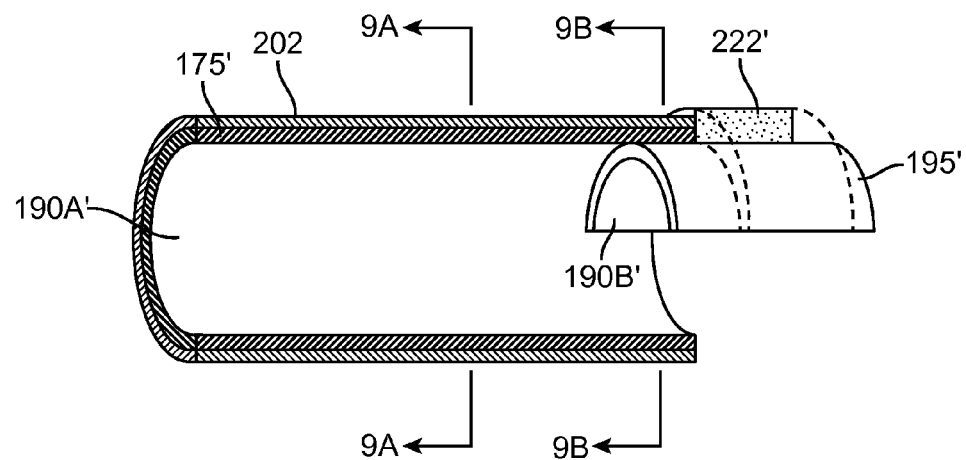
FIG. 8
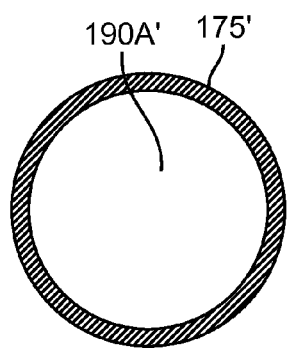
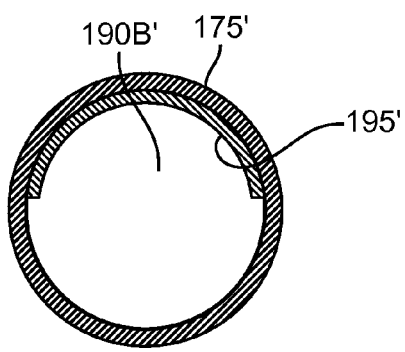
FIG. 9A          FIG. 9B

TISSUE EXTRACTION DEVICES AND METHODS

CROSS-REFERENCE TO RELATED APPLICATIONS

This application is a continuation of U.S. patent application Ser. No. 13/910,873 now U.S. Pat. No. 8,728,066, filed Jun. 5, 2013, which is a divisional of U.S. patent application Ser. No. 13/277,913 now U.S. Pat. No. 8,512,326), filed Oct. 20, 2011, which claims the benefit of U.S. Provisional Application No. 61/501,106, filed on Jun. 24, 2011 and of U.S. Provisional Application No. 61/531,985 filed on Sep. 7, 2011, the full disclosures of which are incorporated herein by reference.

FIELD OF THE INVENTION

The present invention relates systems and methods for the cutting and extraction of uterine fibroid tissue, polyps and other abnormal uterine tissue.

BACKGROUND OF THE INVENTION

Uterine fibroids are non-cancerous tumors that develop in the wall of uterus. Such fibroids occur in a large percentage of the female population, with some studies indicating that up to 40 percent of all women have fibroids. Uterine fibroids can grow over time to be several centimeters in diameter and symptoms can include menorrhagia, reproductive dysfunction, pelvic pressure and pain.

One current treatment of fibroids is hysteroscopic resection or myomectomy which involves transcervical access to the uterus with a hysteroscope together with insertion of a cutting instrument through a working channel in the hysteroscope. The cutting instrument may be a mechanical tissue cutter or an electrosurgical resection device such as a cutting loop. Mechanical cutting devices are disclosed in U.S. Pat. Nos. 7,226,459; 6,032,673 and 5,730,752 and U.S. Published Patent Appl. 2009/0270898. An electrosurgical cutting device is disclosed in U.S. Pat. No. 5,906,615.

While hysteroscopic resection can be effective in removing uterine fibroids, many commercially available instrument are too large in diameter and thus require anesthesia in an operating room environment. Conventional resectoscopes require cervical dilation to about 9 mm. What is needed is a system that can effectively cut and remove fibroid tissue through a small diameter hysteroscope.

SUMMARY OF THE INVENTION

The present invention provides methods for resecting and removing target tissue from a patient's body, such as fibroids from a uterus. The tissue is cut, captured in a probe, catheter, or other tissue-removal device, and expelled from the capture device by vaporizing a fluid, typically a liquid, adjacent to the captured tissue in order to propel the tissue from the device, typically through an extraction or other lumen present in a body or shaft of the device. Exemplary embodiments of the tissue removal device comprise a reciprocating blade, tubular cutter, or the like, where the blade may be advanced past a cutting window on the device in order to sever a tissue strip and capture the strip within an interior volume or receptacle on the device. The liquid or other expandable fluid is also present in the device, and energy is applied to the fluid in order to cause rapid expansion, e.g. vaporization, in order to propel the severed tissue strip through the extraction lumen. In this way, the dimensions of the extraction lumen can be reduced, particularly in the distal regions of the device where size is of critical importance.

In a first method, according to the present invention, tissue is extracted from an interior of the patient's body by capturing a tissue volume in a distal portion of an interior passageway of an elongated probe. A fluid located distal to the captured tissue volume is expanded, which proximally propels the tissue volume from the device. The fluid typically comprises a liquid, and the expansion typically comprises a liquid-to-vapor phase transition. In other cases, the fluid might be a gas where the expansion results from very rapid heating. In preferred embodiments, the phase transition is achieved by applying electrical energy in an amount sufficient to vaporize the liquid, typically applying RF current between first and second polarity electrodes, where at least one of the electrodes is disposed on a distal side of the captured tissue volume.

The liquid or other fluid may be provided to a working end of the probe in various ways. Often, the liquid or other fluid is provided from a fluid-filled space in the patient's body, for example from a distension fluid filled in the cavity to be treated, such as the uterus. Alternatively, the liquid or other fluid may be provided from a remote source through a passageway in the probe. The liquid volume to be vaporized is typically in the range from 0.004 mL to 0.080 mL.

The tissue may be captured in a variety of ways. For example, the tissue may be resected with a blade number or alternatively with an RF electrode. In either case, the resected tissue may then be captured or sequestered within an interior passageway within the blade itself and/or within another portion of the probe. In addition to the propulsion force caused by the vaporizing fluid, the present invention might also rely on applying a negative pressure to a proximal end of the anterior passageway to assist in drawing the tissue in a proximal direction from the extraction lumen.

In a further method according to the present invention, tissue is removed from the interior of a patient's body by engaging a tubular cutter against the targeted tissue. An RF electrode arrangement on the cutter is energized to electrosurgically cut the tissue, and the same or a different RF electrode is used to vaporize a liquid to apply a positive fluid pressure to a distal surface of the cut tissue. Usually, the same RF electrode arrangement is used to both electrosurgically cut the tissue and to vaporize the liquid. In such instances, the cutter carrying the RF electrode is usually first advanced to electrosurgically cut the tissue and thereafter advanced into the liquid to vaporize the liquid. The liquid is usually present in a chamber or other space having an active electrode at a distal end thereof, and the RF electrode arrangement on the cutter comprises a return electrode. In this way, with the smaller active electrode on the distal side of the tissue, the energy which vaporizes the liquid will be concentrated in the chamber on the distal side of the tissue, thus causing rapid vaporization of the liquid and propulsion of the tissue through the extraction lumen.

In a third method according to the present invention, tissue is cut and extracted from the interior of a patient's body by reciprocating a cutting member within a tubular cutter body to sever a tissue strip. The severed tissue strip is captured in an extraction lumen of the tubular cutter body, and a phase transition is caused in a fluid distal to the tissue strip to thereby apply a proximally directed expelling or propulsion force to the tissue strip. The phase transition may be caused by applying energy from any one of a variety of energy sources, including an ultrasound transducer, a high-intensity focused ultrasound (HIFU) energy source, a laser energy source, a light or optical energy source, a microwave energy source, a resistive heat source, or the like. Typically, the cutter will carry the energy source, and the energy source is also used to effect cutting of the tissue. In this way the cutter can also carry the energy source into the fluid after the tissue has been cut, and the cutting and vaporization steps can be performed sequentially as the cutter first moves through the tissue and then into the liquid or other fluid to be vaporized.

In a still further method according to the present invention, tissue is cut and extracted by first cutting the tissue with a reciprocating cutting member over an extending stroke and a retracting stroke within a sleeve. The extending stroke cuts and captures tissue which has been drawn through a tissue-receiving window in the sleeve. Vaporization of a liquid distal to the captured tissue is caused by the cutting member while the cutting member is in a transition range between extension and retraction. The tissue is typically captured in the tissue extraction lumen formed at least partially in the cutter member. The cutter member typically carries a cutting electrode, and a second electrode is typically disposed at a distal end of the sleeve. Thus, RF current may be delivered to the cutting electrode and the second electrode in order to both effect cutting of the tissue over the extending stroke of the cutter and to also effect vaporization of the fluid while the cutter is in the transition range.

BRIEF DESCRIPTION OF DRAWINGS

FIG. 8 is a schematic view of a distal end portion of another embodiment of inner RF cutting sleeve.

FIG. 9A is a cross sectional view of the RF cutting sleeve of FIG. 8 taken along line 9A-9A of FIG. 8.

FIG. 9B is a cross sectional view of the RF cutting sleeve of FIG. 8 taken along line 9B-9B of FIG. 8.

DETAILED DESCRIPTION OF THE INVENTION

Figure 1:
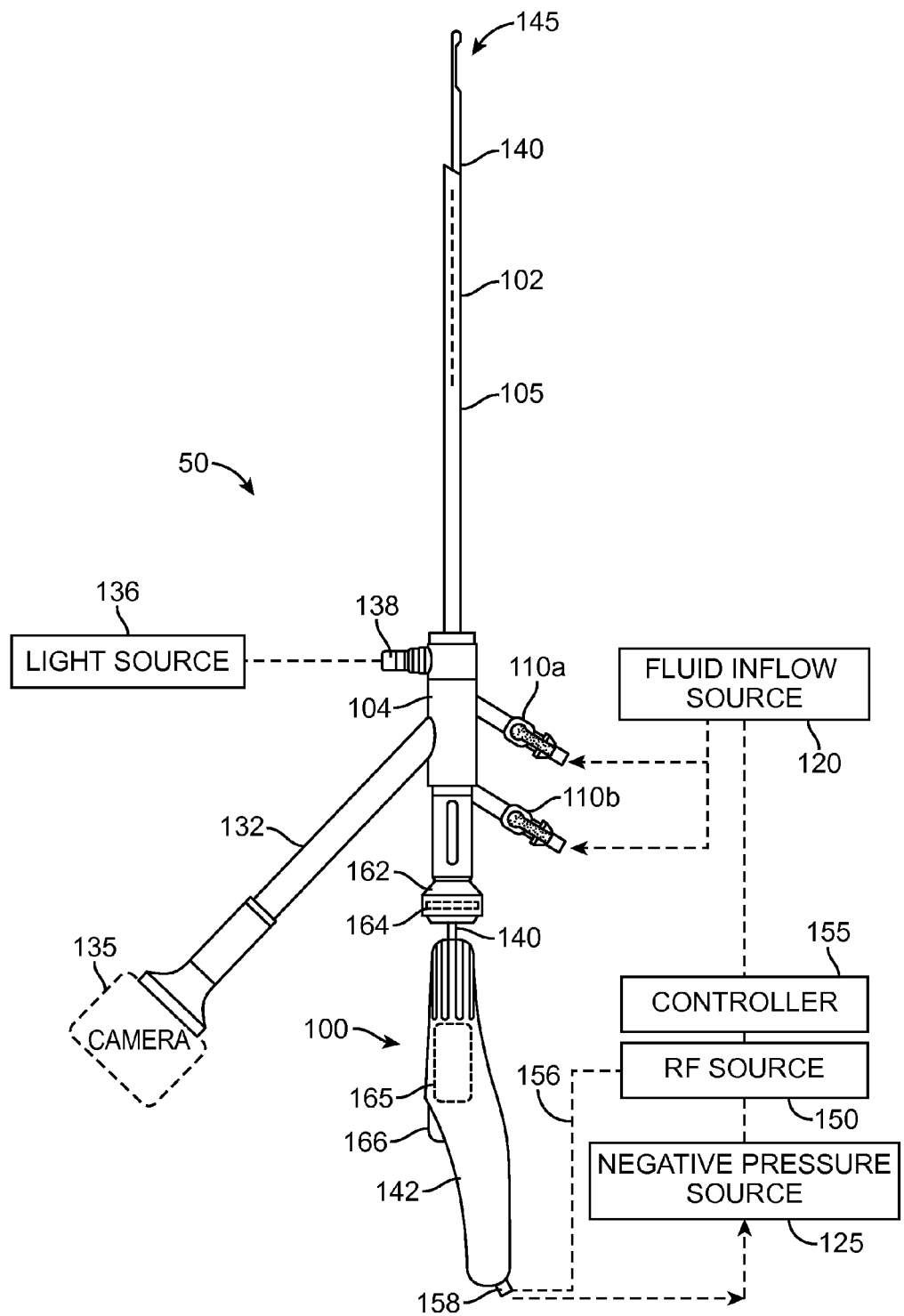
FIG. 1 is a plan view of an assembly including a hysteroscope and a tissue-cutting device corresponding to the invention that is inserted through a working channel of the hysteroscope.
Figure 2:
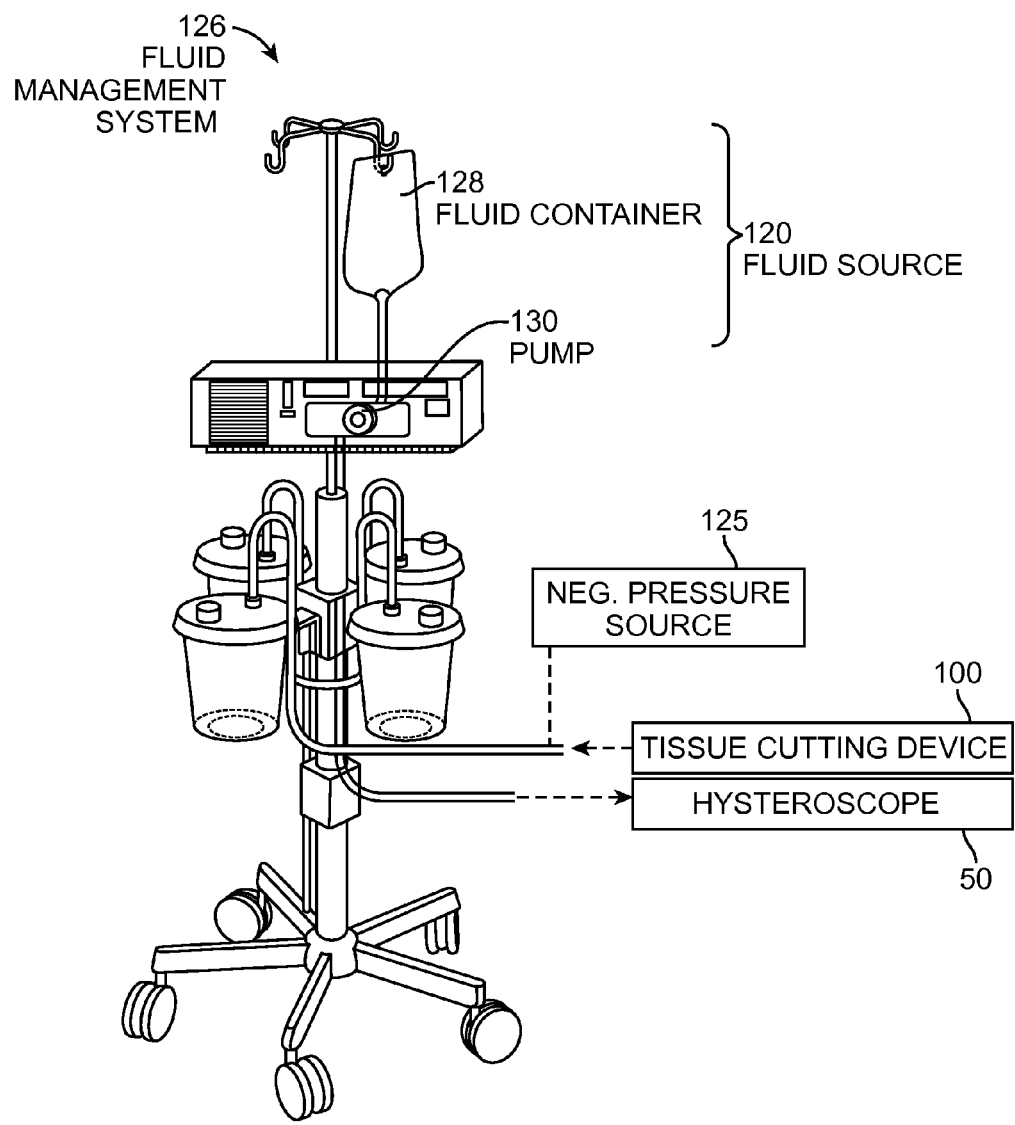
FIG. 2 is a schematic perspective view of a fluid management system used for distending the uterus and for assisting in electrosurgical tissue cutting and extraction.
Figure 3:
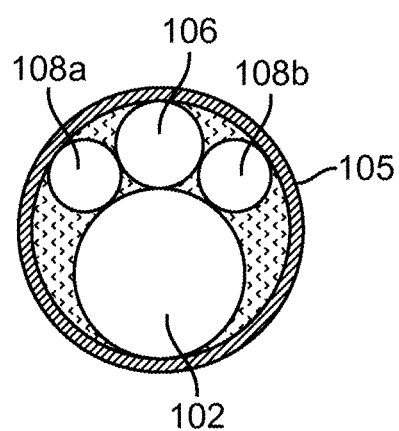
FIG. 3 is a cross-sectional view of the shaft of the hysteroscope of FIG. 1 showing various channels therein.

FIG. 1 illustrates an assembly that comprises an endoscope 50 used for hysteroscopy together with a tissue-extraction device 100 extending through a working channel 102 of the endoscope. The endoscope or hysteroscope 50 has a handle 104 coupled to an elongated shaft 105 having a diameter of 5 mm to 7 mm. The working channel 102 therein may be round, D-shaped or any other suitable shape. The endoscope shaft 105 is further configured with an optics channel 106 and one or more fluid inflow/outflow channels 108a, 108b (FIG. 3) that communicate with valve-connectors 110a, 110b configured for coupling to a fluid inflow source 120 thereto, or optionally a negative pressure source 125 (FIGS. 1-2). The fluid inflow source 120 is a component of a fluid management system 126 as is known in the art (FIG. 2) which comprises a fluid container 128 and pump mechanism 130 which pumps fluid through the hysteroscope 50 into the uterine cavity. As can be seen in FIG. 2, the fluid management system 126 further includes the negative pressure source 125 (which can comprise an operating room wall suction source) coupled to the tissue-cutting device 100. The handle 104 of the endoscope includes the angled extension portion 132 with optics to which a videoscopic camera 135 can be operatively coupled. A light source 136 also is coupled to light coupling 138 on the handle of the hysteroscope 50. The working channel 102 of the hysteroscope is configured for insertion and manipulation of the tissue-cutting and extracting device 100, for example to treat and remove fibroid tissue. In one embodiment, the hysteroscope shaft 105 has an axial length of 21 cm, and can comprise a 0° scope, or 15° to 30° scope.

Still referring to FIG. 1, the tissue-cutting device 100 has a highly elongated shaft assembly 140 configured to extend through the working channel 102 in the hysteroscope. A handle 142 of the tissue-cutting device 100 is adapted for manipulating the electrosurgical working end 145 of the device. In use, the handle 142 can be manipulated both rotationally and axially, for example, to orient the working end 145 to cut targeted fibroid tissue. The tissue-cutting device 100 has subsystems coupled to its handle 142 to enable electrosurgical cutting of targeted tissue. A radiofrequency generator or RF source 150 and controller 155 are coupled to at least one RF electrode carried by the working end 145 as will be described in detail below. In one embodiment shown in FIG. 1, an electrical cable 156 and negative pressure source 125 are operatively coupled to a connector 158 in handle 142. The electrical cable couples the RF source 150 to the electrosurgical working end 145. The negative pressure source 125 communicates with a tissue-extraction channel 160 in the shaft assembly 140 of the tissue extraction device 100 (FIG. 4).

FIG. 1 further illustrates a seal housing 162 that carries a flexible seal 164 carried by the hysteroscope handle 104 for sealing the shaft 140 of the tissue-cutting device 100 in the working channel 102 to prevent distending fluid from escaping from a uterine cavity.

In one embodiment as shown in FIG. 1, the handle 142 of tissue-cutting device 100 includes a motor drive 165 for reciprocating or otherwise moving a cutting component of the electrosurgical working end 145 as will be described below. The handle 142 optionally includes one or more actuator buttons 166 for actuating the device. In another embodiment, a footswitch can be used to operate the device. In one embodiment, the system includes a switch or control mechanism to provide a plurality of reciprocation speeds, for example 1 Hz, 2 Hz, 3 Hz, 4 Hz and up to 8 Hz. Further, the system can include a mechanism for moving and locking the reciprocating cutting sleeve in a non-extended position and in an extended position. Further, the system can include a mechanism for actuating a single reciprocating stroke.

Figure 4:
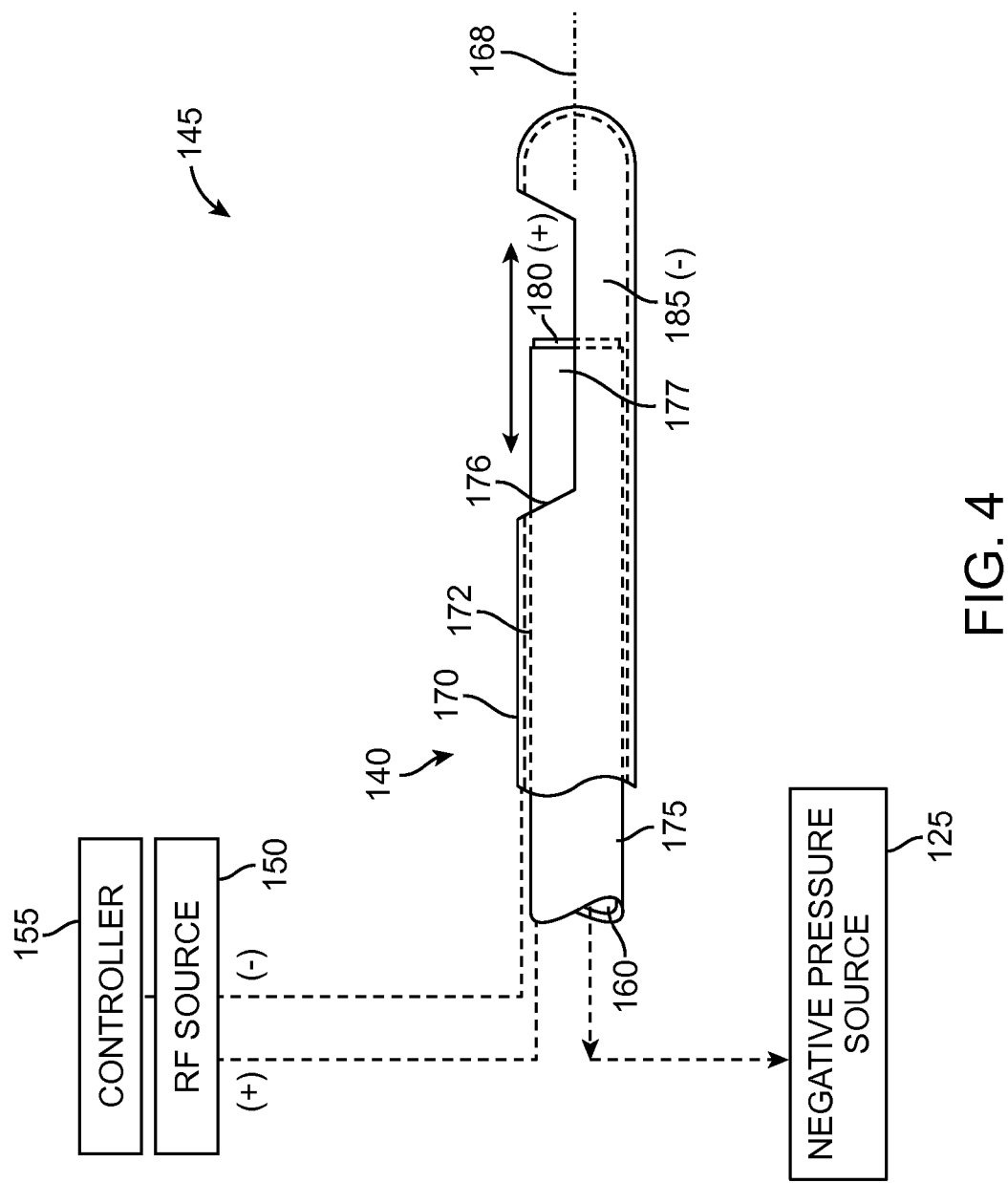
FIG. 4 is a schematic side view of the working end of the electrosurgical tissue-cutting device of FIG. 1 showing an outer sleeve and a reciprocating inner sleeve and an electrode arrangement.

Referring to FIGS. 1 and 4, an electrosurgical tissue-cutting device has an elongate shaft assembly 140 extending about longitudinal axis 168 comprising an exterior or first outer sleeve 170 with passageway or lumen 172 therein that accommodates a second or inner sleeve 175 that can reciprocate (and optionally rotate or oscillate) in lumen 172 to cut tissue as is known in that art of such tubular cutters. In one embodiment, the tissue-receiving window 176 in the outer sleeve 170 has an axial length ranging between 10 mm and 30 mm and extends in a radial angle about outer sleeve 170 from about 45° to 210° relative to axis 168 of the sleeve. The outer and inner sleeves 170 and 175 can comprise a thin-wall stainless steel material and function as opposing polarity electrodes as will be described in detail below. FIGS. 6A-8 illustrate insulative layers carried by the outer and inner sleeves 170 and 175 to limit, control and/or prevent unwanted electrical current flows between certain portions of the sleeve. In one embodiment, a stainless steel outer sleeve 170 has an O.D. of 0.143" with an I.D. of 0.133" and with an inner insulative layer (described below) the sleeve has a nominal I.D. of 0.125". In this embodiment, the stainless steel inner sleeve 175 has an O.D. of 0.120" with an I.D. of 0.112". The inner sleeve 175 with an outer insulative layer has a nominal O.D. of about 0.123" to 0.124" to reciprocate in lumen 172. In other embodiments, outer and or inner sleeves can be fabricated of metal, plastic, ceramic of a combination thereof. The cross-section of the sleeves can be round, oval or any other suitable shape.

As can be seen in FIG. 4, the distal end 177 of inner sleeve 175 comprises a first polarity electrode with distal cutting electrode edge 180 about which plasma can be generated. The electrode edge 180 also can be described as an active electrode during tissue cutting since the electrode edge 180 then has a substantially smaller surface area than the opposing polarity or return electrode. In one embodiment in FIG. 4, the exposed surfaces of outer sleeve 170 comprises the second polarity electrode 185, which thus can be described as the return electrode since during use such an electrode surface has a substantially larger surface area compared to the functionally exposed surface area of the active electrode edge 180.

Figure 5:
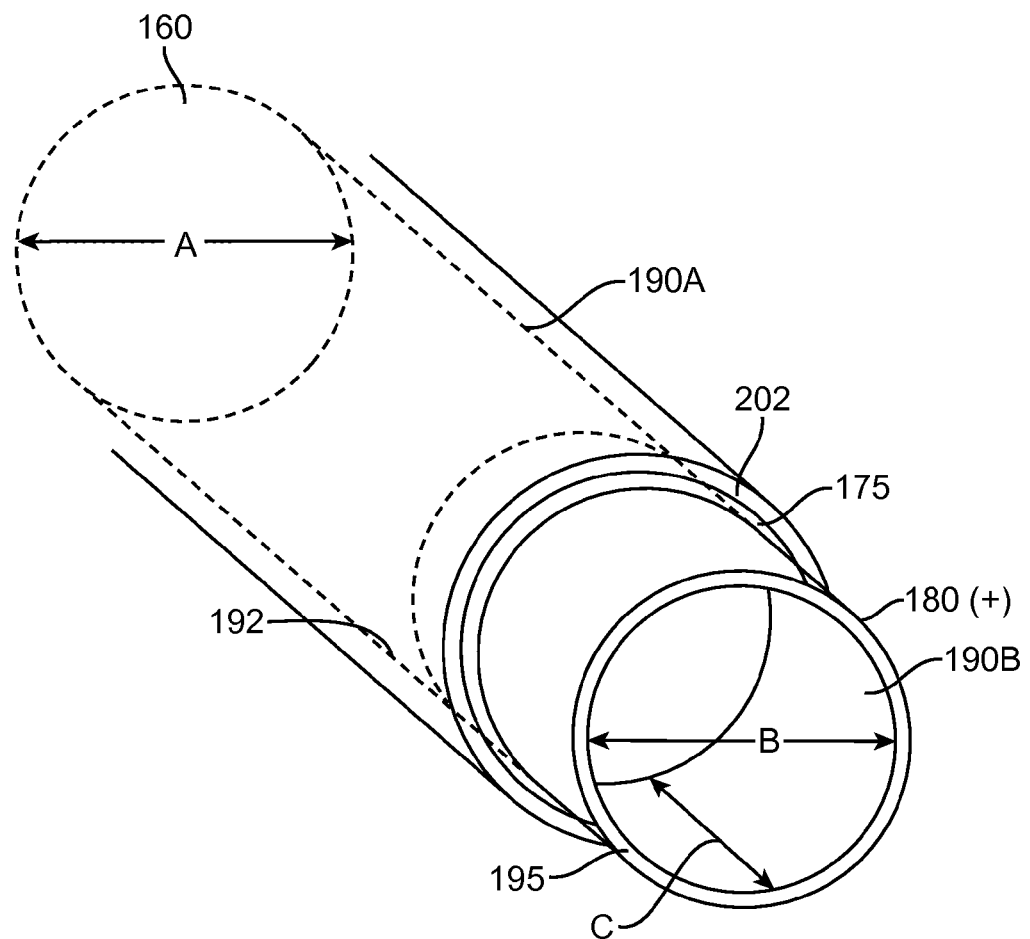
FIG. 5 is a schematic perspective view of the working end of the inner sleeve of FIG. 4 showing its electrode edge.
Figure 6A:
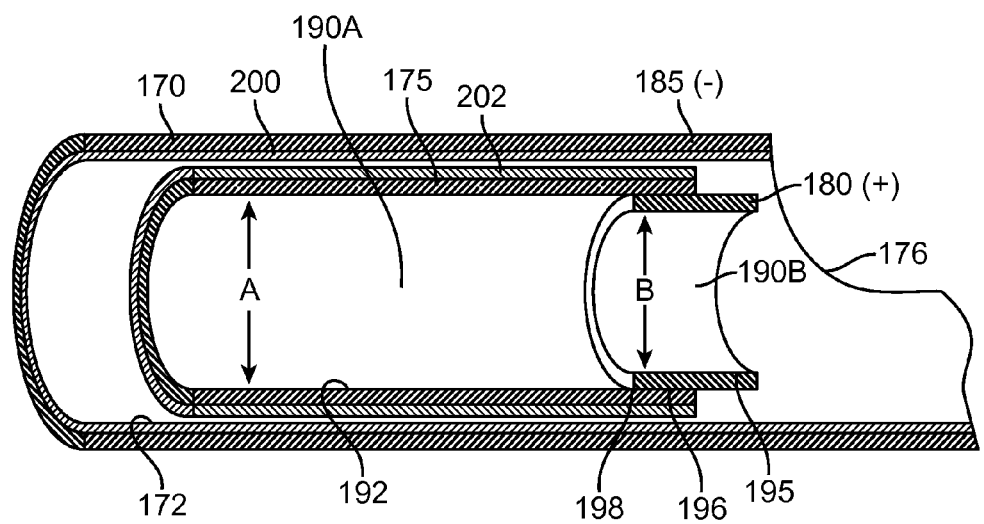
FIG. 6A is a schematic cut-away view of a portion of outer sleeve, inner RF cutting sleeve and a tissue-receiving window of the outer sleeve.

In one aspect of the invention, the inner sleeve or cutting sleeve 175 has an interior tissue extraction lumen 160 with first and second interior diameters that are adapted to electrosurgically cut tissue volumes rapidly—and thereafter consistently extract the cut tissue strips through the highly elongated lumen 160 without clogging. Now referring to FIGS. 5 and 6A, it can be seen that the inner sleeve 175 has a first diameter portion 190A that extends from the handle 142 (FIG. 1) to a distal region 192 of the sleeve 175 wherein the tissue extraction lumen transitions to a smaller second diameter lumen 190B with a reduced diameter indicated at B which is defined by the electrode sleeve element 195 that provides cutting electrode edge 180. The axial length C of the reduced cross-section lumen 190B can range from about 2 mm to 20 mm. In one embodiment, the first diameter A is 0.112" and the second reduced diameter B is 0.100". As shown in FIG. 5, the inner sleeve 175 can be an electrically conductive stainless steel and the reduced diameter electrode portion also can comprise a stainless steel electrode sleeve element 195 that is welded in place by weld 196 (FIG. 6A). In another alternative embodiment, the electrode and reduced diameter electrode sleeve element 195 comprises a tungsten tube that can be press fit into the distal end 198 of inner sleeve 175. FIGS. 5 and 6A further illustrates the interfacing insulation layers 202 and 204 carried by the first and second sleeves 170, 175, respectively. In FIG. 6A, the outer sleeve 170 is lined with a thin-wall insulative material 200, such as PFA, or another material described below. Similarly, the inner sleeve 175 has an exterior insulative layer 202. These coating materials can be lubricious as well as electrically insulative to reduce friction during reciprocation of the inner sleeve 175.

The insulative layers 200 and 202 described above can comprise a lubricious, hydrophobic or hydrophilic polymeric material. For example, the material can comprise a bio-compatible material such as PFA, TEFLON®, polytetrafluoroethylene (PTFE), FEP (Fluorinated ethylenepropylene), polyethylene, polyamide, ECTFE (Ethylenechlorotrifluoroethylene), ETFE, PVDF, polyvinyl chloride or silicone.

Figure 6B:
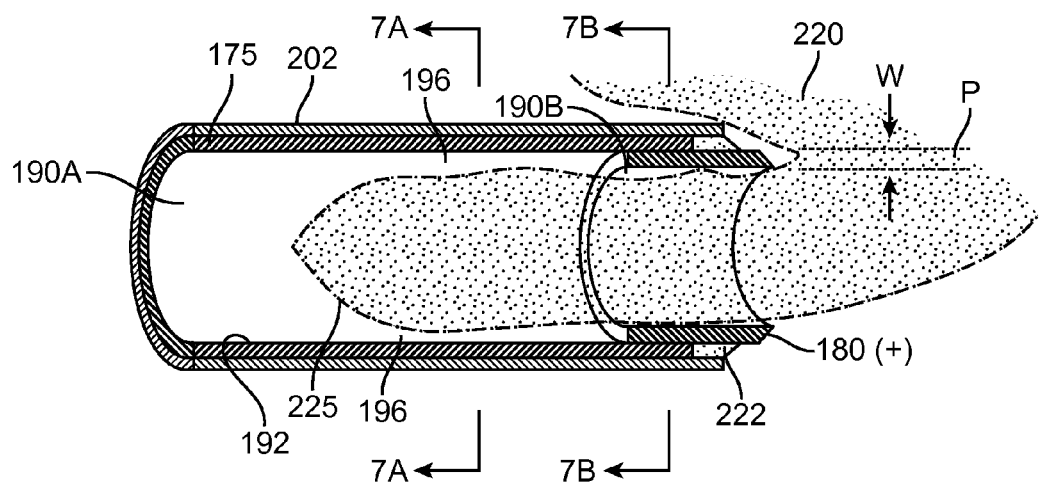
FIG. 6B is a schematic view of a distal end portion another embodiment of inner RF cutting sleeve.

Now turning to FIG. 6B, another variation of inner sleeve 175 is illustrated in a schematic view together with a tissue volume being resected with the plasma electrode edge 180. In this embodiment, as in other embodiments in this disclosure, the RF source operates at selected operational parameters to create a plasma around the electrode edge 180 of electrode sleeve 195 as is known in the art. Thus, the plasma generated at electrode edge 180 can cut and ablate a path P in the tissue 220, and is suited for cutting fibroid tissue and other abnormal uterine tissue. In FIG. 6B, the distal portion of the cutting sleeve 175 includes a ceramic collar 222 which is adjacent the distal edge 180 of the electrode sleeve 195. The ceramic 222 collar functions to confine plasma formation about the distal electrode edge 180 and functions further to prevent plasma from contacting and damaging the polymer insulative layer 202 on the cutting sleeve 175 during operation. In one aspect of the invention, the path P cut in the tissue 220 with the plasma at electrode edge 180 provides a path P having an ablated width indicated at W, wherein such path width W is substantially wide due to tissue vaporization. This removal and vaporization of tissue in path P is substantially different than the effect of cutting similar tissue with a sharp blade edge, as in various prior art devices. A sharp blade edge can divide tissue (without cauterization) but applies mechanical force to the tissue and may prevent a large cross section slug of tissue from being cut. In contrast, the plasma at the electrode edge 180 can vaporize a path P in tissue without applying any substantial force on the tissue to thus cut larger cross sections of slugs or strips of tissue. Further, the plasma cutting effect reduces the cross section of tissue strip 225 received in the reduced cross-section region 190B of tissue-extraction lumen 160. FIG. 6B depicts a tissue strip 225 entering the reduced cross-section region 190B, wherein the tissue strip 225 has a smaller cross-section than the lumen due to the vaporization of tissue. Further, the cross section of tissue 225 as it enters the larger cross-section lumen 190A results in even greater free space 196 around the tissue strip 225. Thus, the resection of tissue with the plasma electrode edge 180, together with the lumen transition from the smaller cross-section (190B) to the larger cross-section (190A) of the tissue-extraction lumen 160 can significantly reduce or eliminate the potential for successive resected tissue strips 225 to clog the lumen. Prior art resection devices with such small diameter tissue-extraction lumen typically have problems with tissue clogging.

In another aspect of the invention, the negative pressure source 225 coupled to the proximal end of tissue-extraction lumen 160 (see FIGS. 1 and 4) also assists in aspirating and moving tissue strips 225 in the proximal direction to a collection reservoir (not shown) outside the handle 142 of the device.

Figure 7A:
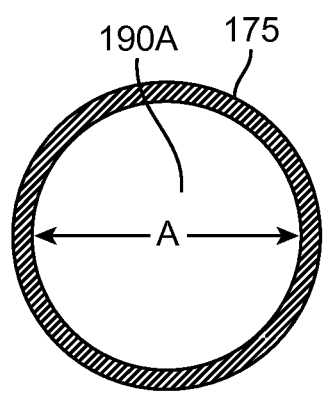
FIG. 7A is a cross sectional view of the inner RF cutting sleeve of FIG. 6B taken along line 7A-7A of FIG. 6B.
Figure 7B:
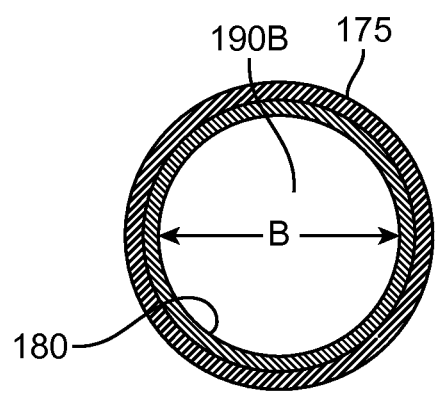
FIG. 7B is another cross sectional view of the inner RF cutting sleeve of FIG. 6B taken along line 7B-7B of FIG. 6B.

FIGS. 7A-7B illustrate the change in lumen diameter of cutting sleeve 175 of FIG. 6B. FIG. 8 illustrates the distal end of a variation of cutting sleeve 175' which is configured with an electrode cutting element 195' that is partially tubular in contrast to the previously described tubular electrode element 195 (FIGS. 5 and 6A). FIGS. 9A-9B again illustrate the change in cross-section of the tissue-extraction lumen between reduced cross-section region 190B' and the increased cross-section region 190A' of the cutting sleeve 175' of FIG. 8. Thus, the functionality remains the same whether the cutting electrode element 195' is tubular or partly tubular. In FIG. 8A, the ceramic collar 222' is shown, in one variation, as extending only partially around sleeve 175' to cooperate with the radial angle of cutting electrode element 195'. Further, the variation of FIG. 8 illustrates that the ceramic collar 222' has a larger outside diameter than insulative layer 202. Thus, friction may be reduced since the short axial length of the ceramic collar 222' interfaces and slides against the interfacing insulative layer 200 about the inner surface of lumen 172 of outer sleeve 170.

In general, one aspect of the invention comprises a tissue cutting and extracting device (FIGS. 10A-11C) that includes first and second concentric sleeves having an axis and wherein the second (inner) sleeve 175 has an axially-extending tissue-extraction lumen therein, and wherein the second sleeve 175 is moveable between axially non-extended and extended positions relative to a tissue-receiving window 176 in first sleeve 170 to resect tissue, and wherein the tissue extraction lumen 160 has first and second cross-sections. The second sleeve 175 has a distal end configured as a plasma electrode edge 180 to resect tissue disposed in tissue-receiving window 176 of the first sleeve 170. Further, the distal end of the second sleeve, and more particularly, the electrode edge 180 is configured for plasma ablation of a substantially wide path in the tissue. In general, the tissue-extraction device is configured with a tissue extraction lumen 160 having a distal end portion with a reduced cross-section that is smaller than a cross-section of medial and proximal portions of the lumen 160.

In one aspect of the invention, referring to FIGS. 7A-7B and 9A-9B, the tissue-extraction lumen 160 has a reduced cross-sectional area in lumen region 190B proximate the plasma cutting tip or electrode edge 180 wherein said reduced cross section is less than 95%, 90%, 85% or 80% of the cross sectional area of medial and proximal portions 190A of the tissue-extraction lumen, and wherein the axial length of the tissue-extraction lumen is at least 10 cm, 20 cm, 30 cm or 40 cm. In one embodiment of tissue-cutting device 100 for hysteroscopic fibroid cutting and extraction (FIG. 1), the shaft assembly 140 of the tissue-cutting device is 35 cm in length.

Figure 10A:
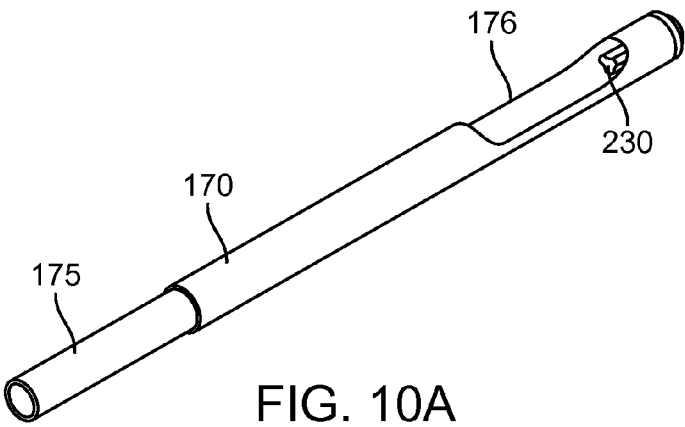
FIG. 10A is a perspective view of the working end of the tissue-cutting device of FIG. 1 with the reciprocating RF cutting sleeve in a non-extended position.
Figure 10B:
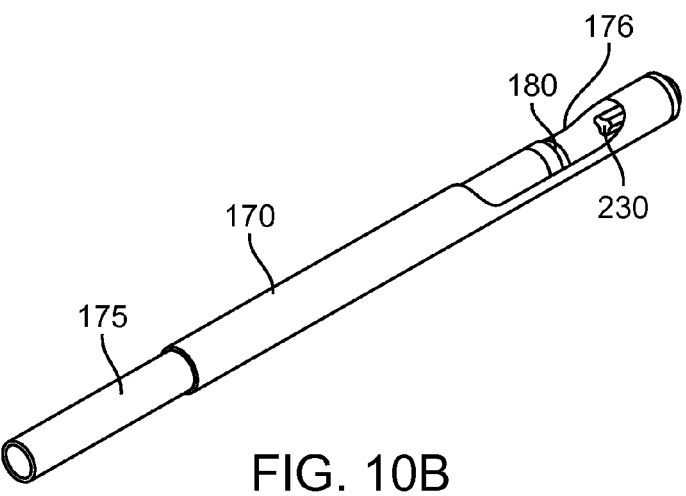
FIG. 10B is a perspective view of the tissue-cutting device of FIG. 1 with the reciprocating RF cutting sleeve in a partially extended position.
Figure 10C:
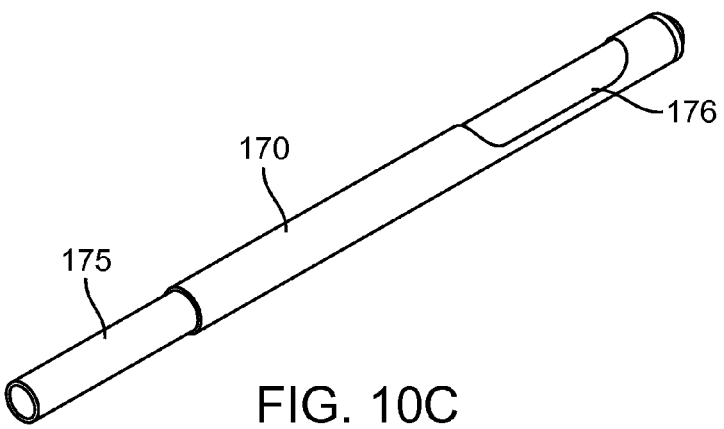
FIG. 10C is a perspective view of the tissue-cutting device of FIG. 1 with the reciprocating RF cutting sleeve in a fully extended position across the tissue-receiving window.
Figure 11A:
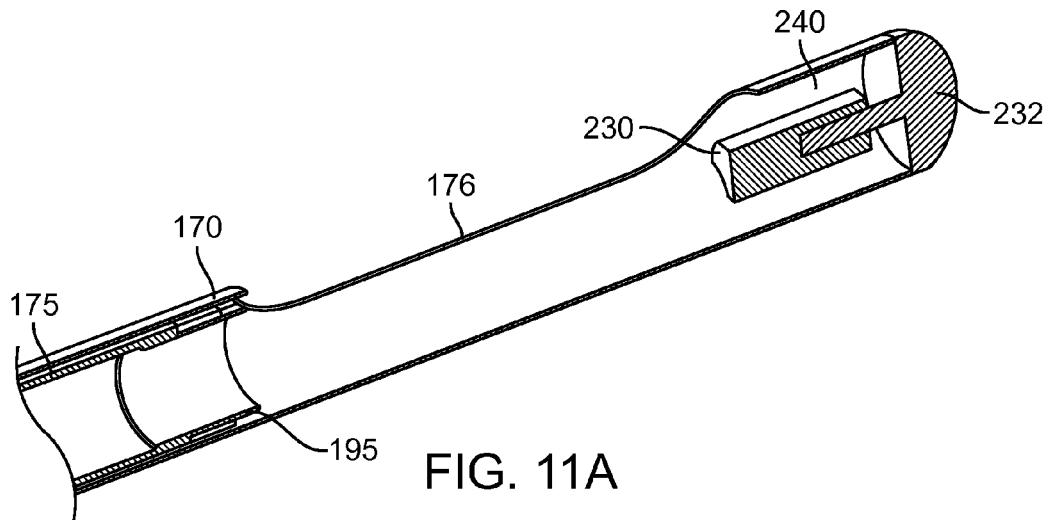
FIG. 11A is a sectional view of the working end of the tissue-cutting device of FIG. 10A with the reciprocating RF cutting sleeve in a non-extended position.
Figure 11B:
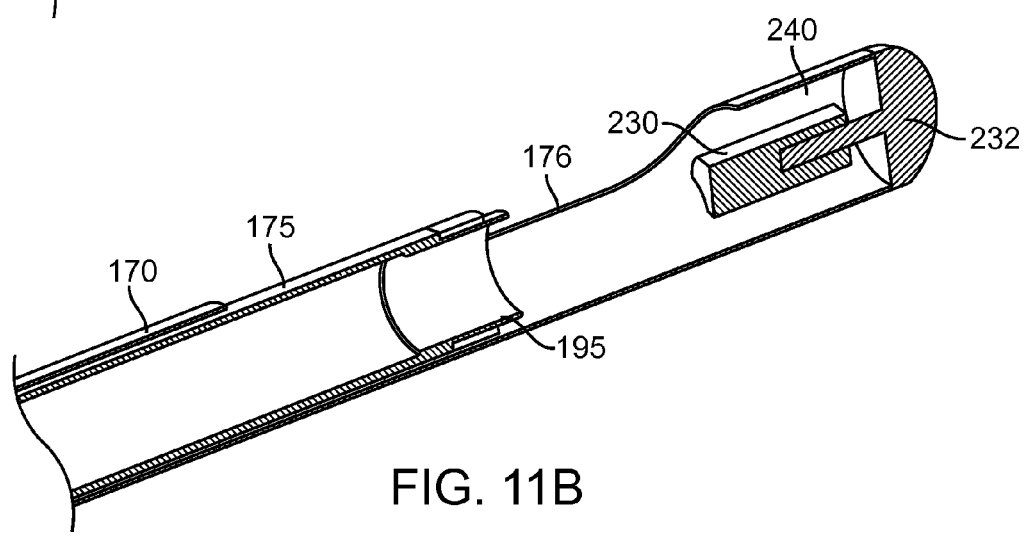
FIG. 11B is a sectional view of the working end of FIG. 10B with the reciprocating RF cutting sleeve in a partially extended position.
Figure 11C:
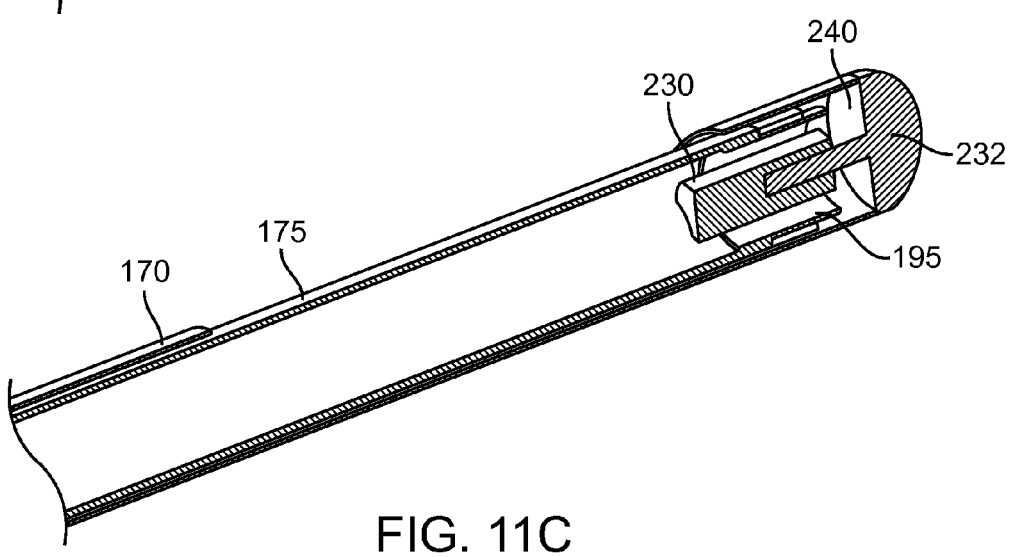
FIG. 11C is a sectional view of the working end of FIG. 10C with the reciprocating RF cutting sleeve in a fully extended position.

FIGS. 10A-10C illustrate the working end 145 of the tissue-cutting device 100 with the reciprocating cutting sleeve or inner sleeve 175 in three different axial positions relative to the tissue receiving window 176 in outer sleeve 170. In FIG. 10 A, the cutting sleeve 175 is shown in a retracted or non-extended position in which the sleeve 175 is at it proximal limit of motion and is prepared to advance distally to an extended position to thereby electrosurgically cut tissue positioned in and/or suctioned into window 176. FIG. 10B shows the cutting sleeve 175 moved and advanced distally to a partially advanced or medial position relative to tissue cutting window 176. FIG. 10C illustrates the cutting sleeve 175 fully advanced and extended to the distal limit of its motion wherein the plasma cutting electrode 180 has extended past the distal end 226 of tissue-receiving window 176 at which moment the resected tissue strip 225 in excised from tissue volume 220 and captured in reduced cross-sectional lumen region 190B.

Now referring to FIGS. 10A-10C, FIGS. 11A-11C and FIGS. 12A-12C, another aspect of the invention comprises "tissue displacement" mechanisms provided by multiple elements and processes to "displace" and move tissue strips 225 (FIG. 12A) in the proximal direction in lumen 160 of cutting sleeve 175 to thus ensure that tissue does not clog the lumen of the inner sleeve 175. As can seen in FIG. 10A and the enlarged views of FIGS. 11A-11C, one tissue displacement mechanism comprises a projecting element 230 that extends proximally from distal tip 232 which is fixedly attached to outer sleeve 170. The projecting element 230 extends proximally along central axis 168 in a distal chamber 240 defined by outer sleeve 170 and distal tip 232. In one embodiment depicted in FIG. 11A, the shaft-like projecting element 230, in a first functional aspect, comprises a mechanical pusher that functions to push a captured tissue strip 225 proximally from the small cross-section lumen 190B of cutting sleeve 175 (FIG. 12A) as the cutting sleeve 175 moves to its fully advanced or extended position.

Figure 12A:
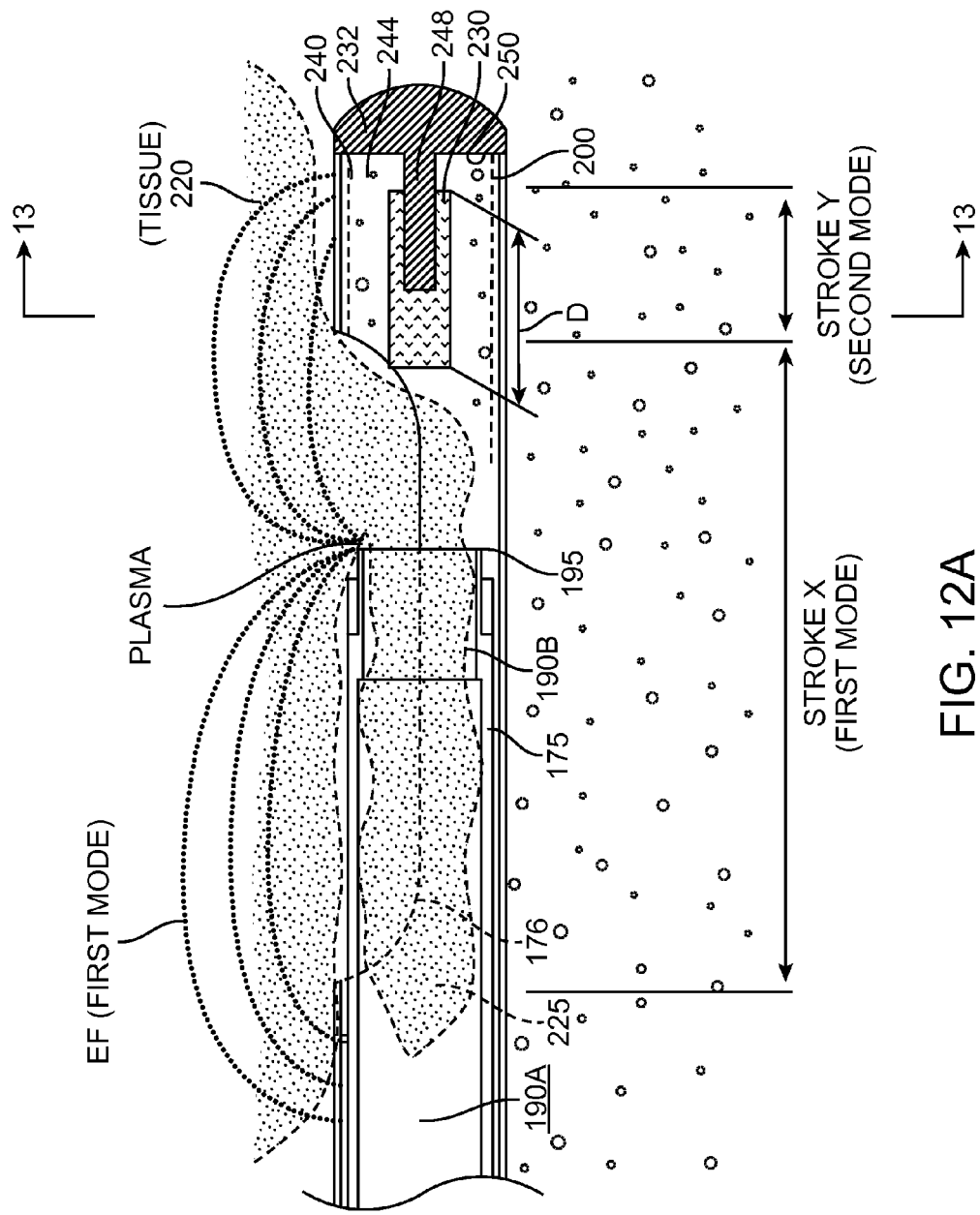
FIG. 12A is an enlarged sectional view of the working end of tissue-cutting device of FIG. 11B with the reciprocating RF cutting sleeve in a partially extended position showing the RF field in a first RF mode and plasma cutting of tissue.
Figure 12B:
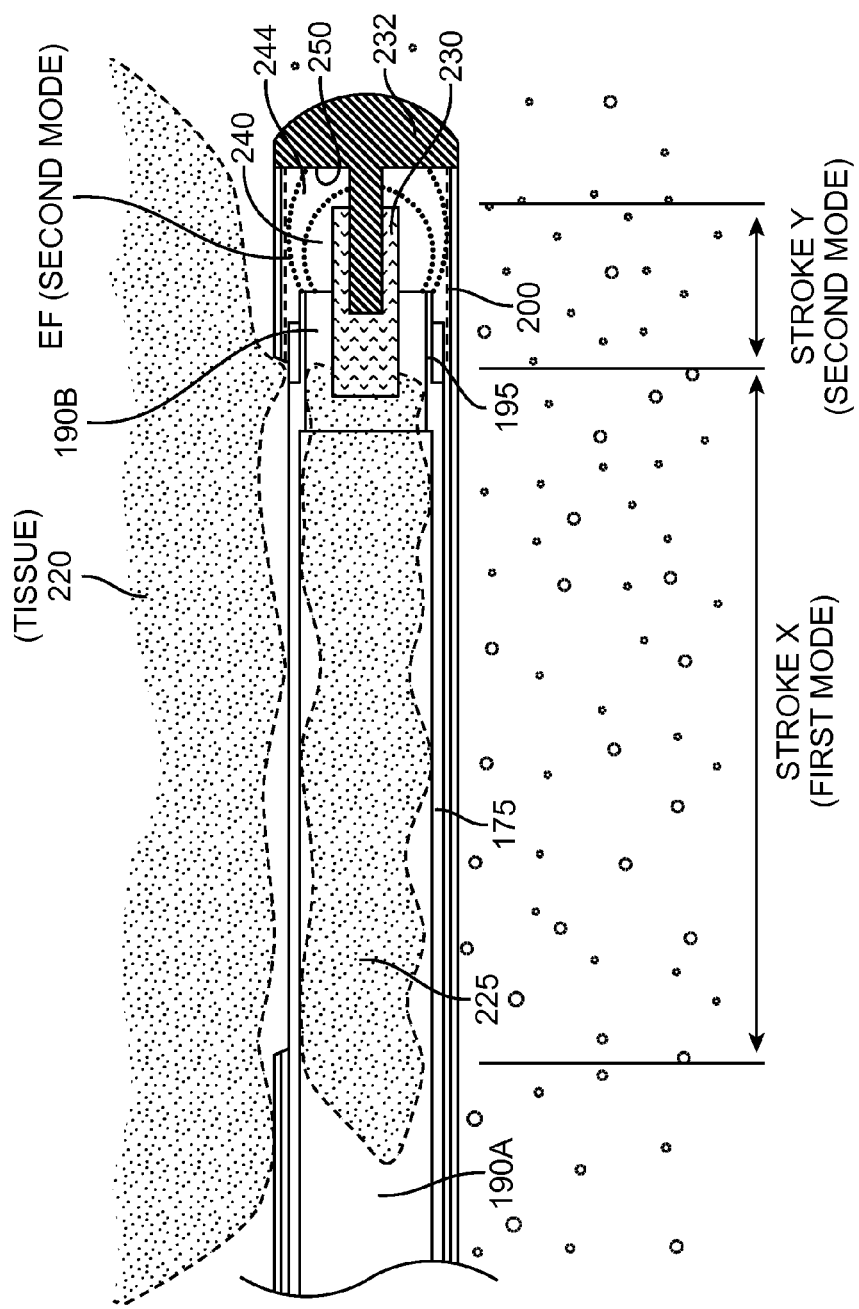
FIG. 12B is an enlarged sectional view of the working end of FIG. 11C with the reciprocating RF cutting sleeve almost fully extended and showing the RF fields switching to a second RF mode from a first RF mode shown in FIG. 12A.
Figure 12C:
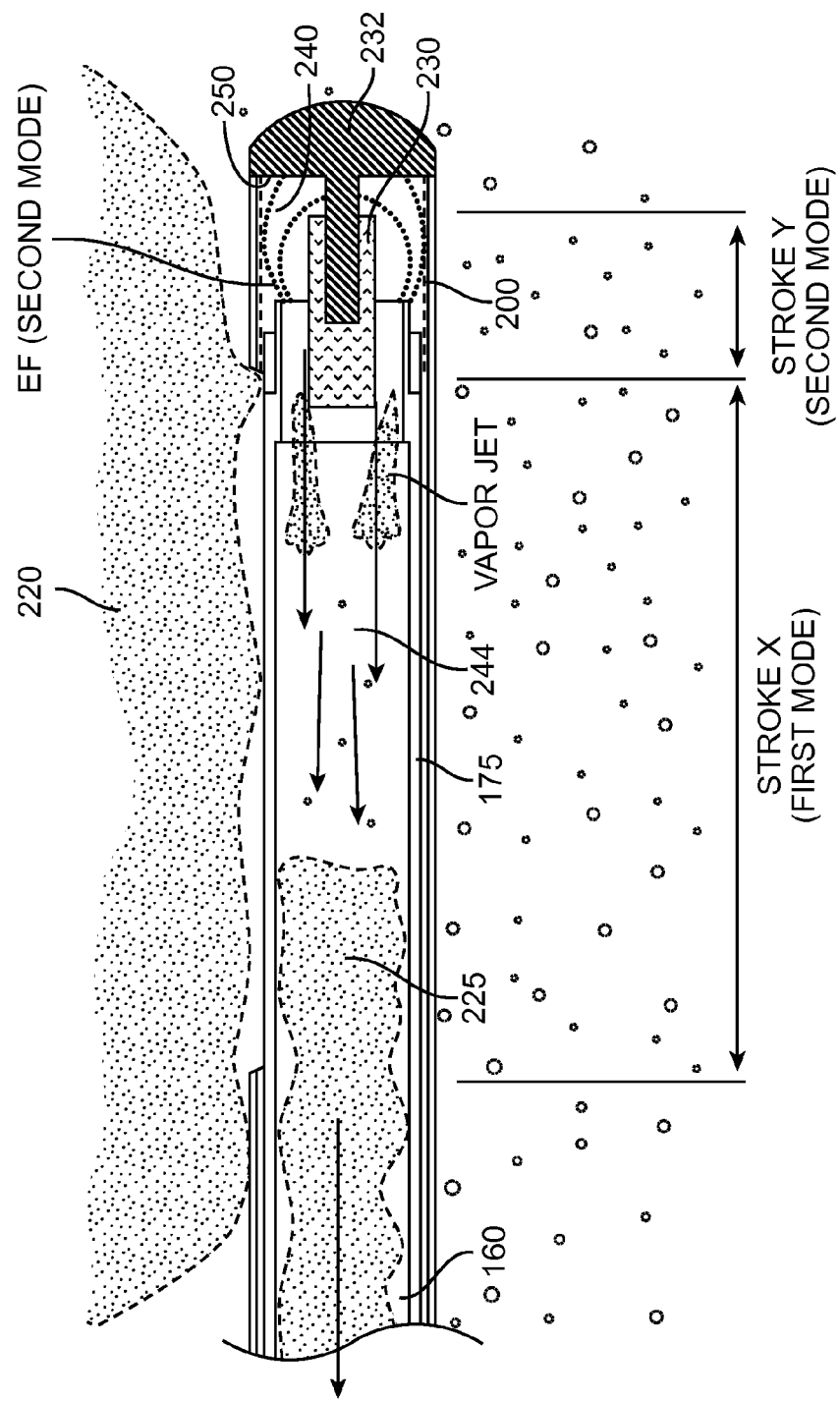
FIG. 12C is an enlarged sectional view of the working end of FIG. 11C with the reciprocating RF cutting sleeve again almost fully extended and showing the explosive vaporization of a captured liquid volume to expel cut tissue in the proximal direction.

In a second functional aspect, the chamber 240 in the distal end of sleeve 170 is configured to capture a volume of saline distending fluid 244 (FIG. 12A) from the working space, and wherein the existing RF electrodes of the working end 145 are further configured to explosively vaporize the captured fluid 244 to generate proximally-directed forces on tissue strips 225 resected and disposed in lumen 160 of the cutting sleeve 175 (FIGS. 12B and 12C). Both of these functional elements and processes (tissue displacement mechanisms) can apply a substantial mechanical force on the captured tissue strips 225 by means of the explosive vaporization of liquid in chamber 240 and can function to move tissue strips 225 in the proximal direction in the tissue-extraction lumen 160. It has been found that using the combination of multiple functional elements and processes can virtually eliminate the potential for tissue clogging the tissue extraction lumen 160.

More particularly, FIGS. 12A-12C illustrate the functional aspects of the tissue displacement mechanisms and the subsequent explosive vaporization of fluid captured in chamber 240. In FIG. 12A, the reciprocating cutting sleeve 175 is shown in a medial position advancing distally wherein plasma at the cutting electrode edge 180 is cutting a tissue strip 225 that is disposed within lumen 160 of the cutting sleeve 175. In FIG. 12A-12C, it can be seen that the system operates in first and second electrosurgical modes corresponding to the reciprocation and axial range of motion of cutting sleeve 175 relative to the tissue-receiving window 176. As used herein, the term "electrosurgical mode" refers to which electrode of the two opposing polarity electrodes functions as an "active electrode" and which electrode functions as a "return electrode". The terms "active electrode" and "return electrode" are used in accordance with convention in the art—wherein an active electrode has a smaller surface area than the return electrode which thus focuses RF energy density about such an active electrode. In the working end 145 of FIGS. 10A-11C, the cutting electrode element 195 and its cutting electrode edge 180 must comprise the active electrode to focus energy about the electrode to generate the plasma for tissue cutting. Such a high-intensity, energetic plasma at the electrode edge 180 is needed throughout stroke X indicated in FIG. 12A-12B to cut tissue. The first mode occurs over an axial length of travel of inner cutting sleeve 175 as it crosses the tissue-receiving window 176, at which time the entire exterior surface of outer sleeve 170 comprises the return electrode indicated at 185. The electrical fields EF of the first RF mode are indicated generally in FIG. 12A.

FIG. 12 B illustrates the moment in time at which the distal advancement or extension of inner cutting sleeve 175 entirely crosses the tissue-receiving window 176 (FIG. 12A). At this time, the electrode sleeve 195 and its electrode edge 180 are confined within the mostly insulated-wall chamber 240 defined by the outer sleeve 170 and distal tip 232. At this moment, the system is configured to switch to the second RF mode in which the electric fields EF switch from those described previously in the first RF mode. As can be seen in FIG. 12B, in this second mode, the limited interior surface area 250 (FIG. 12C) of distal tip 232 that interfaces chamber 240 functions as an active electrode and the distal end portion of cutting sleeve 175 exposed to chamber 240 acts as a return electrode. In this mode, very high energy densities occur about surface 250 and such a contained electric field EF can explosively and instantly vaporize the fluid 244 captured in chamber 240. The expansion of water vapor can be dramatic and can thus apply tremendous mechanical forces and fluid pressure on the tissue strip 225 to move the tissue strip in the proximal direction in the tissue extraction lumen 160. FIG. 12C illustrates such explosive or expansive vaporization of the distention fluid 244 captured in chamber 240 and further shows the tissue strip 225 being expelled in the proximal direction the lumen 160 of inner cutting sleeve 175.

Figure 14:
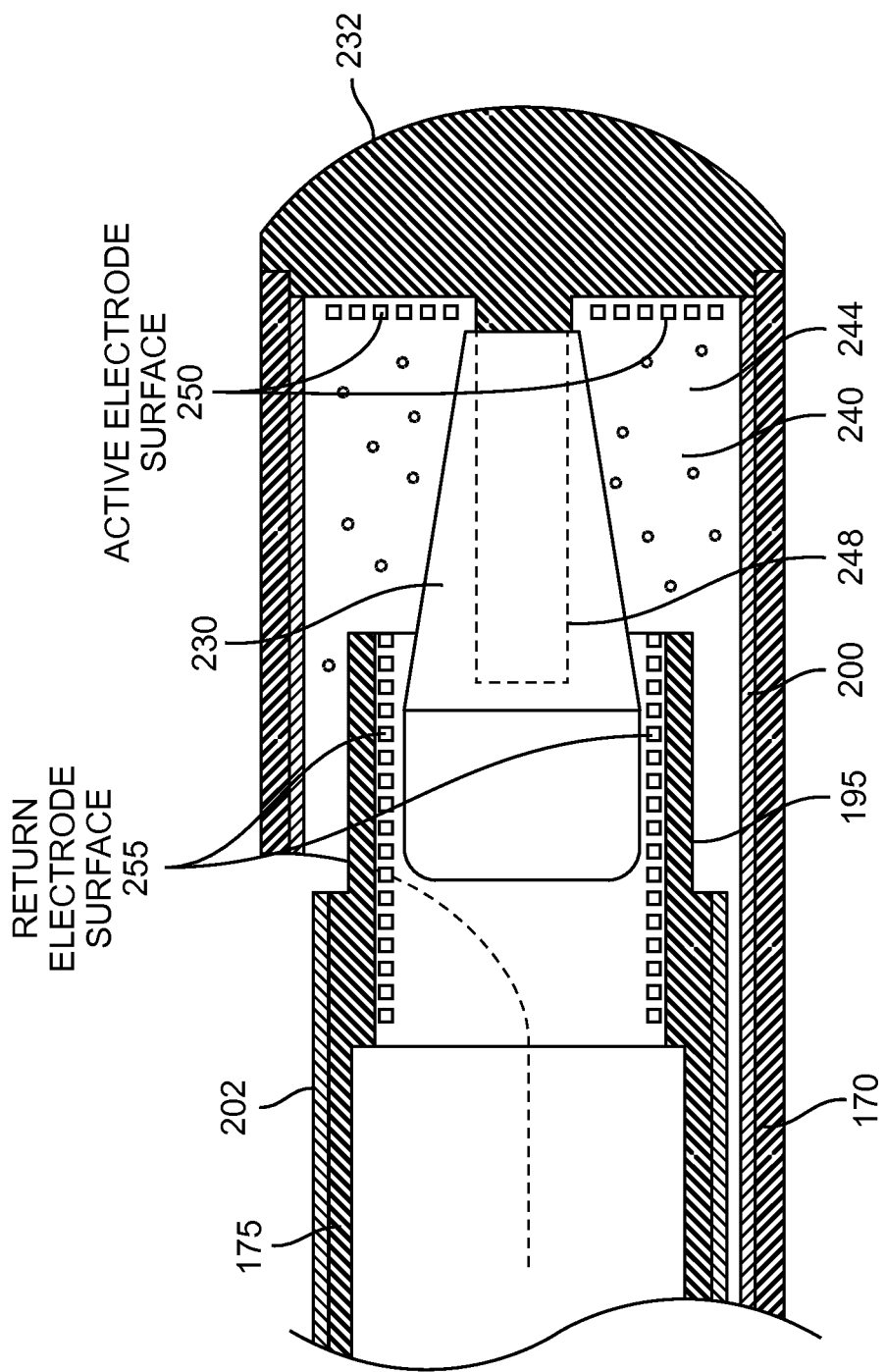
FIG. 14 is a sectional view of the working end of FIG. 12C showing an interior chamber and a variation of a projecting element.

FIG. 14 shows the relative surface areas of the active and return electrodes at the extended range of motion of the cutting sleeve 175, again illustrating that the surface area of the non-insulated distal end surface 250 is small compared to surface 255 of electrode sleeve which comprises the return electrode.

Still referring to FIGS. 12A-12C, it has been found that a single power setting on the RF source 150 and controller 155 can be configured both (i) to create plasma at the electrode cutting edge 180 of electrode sleeve 195 to cut tissue in the first mode, and (ii) to explosively vaporize the captured distention fluid 244 in the second mode. Further, it has been found that the system can function with RF mode-switching automatically at suitable reciprocation rates ranging from 0.5 cycles per second to 8 or 10 cycles per second. In bench testing, it has been found that the tissue-cutting device described above can cut and extract tissue at the rate of from 4 grams/min to 8 grams/min without any potential for tissue strips 225 clogging the tissue-extraction lumen 160. In these embodiments, the negative pressure source 125 also is coupled to the tissue-extraction lumen 160 to assist in applying forces for tissue extraction.

Of particular interest, the fluid-capture chamber 240 defined by sleeve 170 and distal tip 232 can be designed to have a selected volume, exposed electrode surface area, length and geometry to optimize the application of expelling forces to resected tissue strips 225. In one embodiment, the diameter of the chamber is 3.175 mm and the length is 5.0 mm which taking into account the projecting element 230, provided a captured fluid volume of approximately 0.040 mL. In other variations, the captured fluid volume can range from 0.004 mL to 0.080 mL.

In one example, a chamber 240 with a captured liquid volume of 0.040 mL together with 100% conversion efficiency in and instantaneous vaporization would require 103 Joules to heat the liquid from room temperature to water vapor. In operation, since a Joule is a W*s, and the system reciprocate at 3 Hz, the power required would be on the order of 311 W for full, instantaneous conversion to water vapor. A corresponding theoretical expansion of 1700× would occur in the phase transition, which would results in up to 25,000 psi instantaneously (14.7 psi×1700), although due to losses in efficiency and non-instantaneous expansion, the actual pressures would be much less. In any event, the pressures are substantial and can apply significant expelling forces to the captured tissue strips 225.

Referring to FIG. 12A, the interior chamber 240 can have an axial length from about 0.5 mm to 10 mm to capture a liquid volume ranging from about 0.004 mL 0.01 mL. It can be understood in FIG. 12A, that the interior wall of chamber 240 has an insulator layer 200 which thus limits the electrode surface area 250 exposed to chamber 240. In one embodiment, the distal tip 232 is stainless steel and is welded to outer sleeve 170. The post element 248 is welded to tip 232 or machined as a feature thereof. The projecting element 230 in this embodiment is a non-conductive ceramic.

Figure 13:
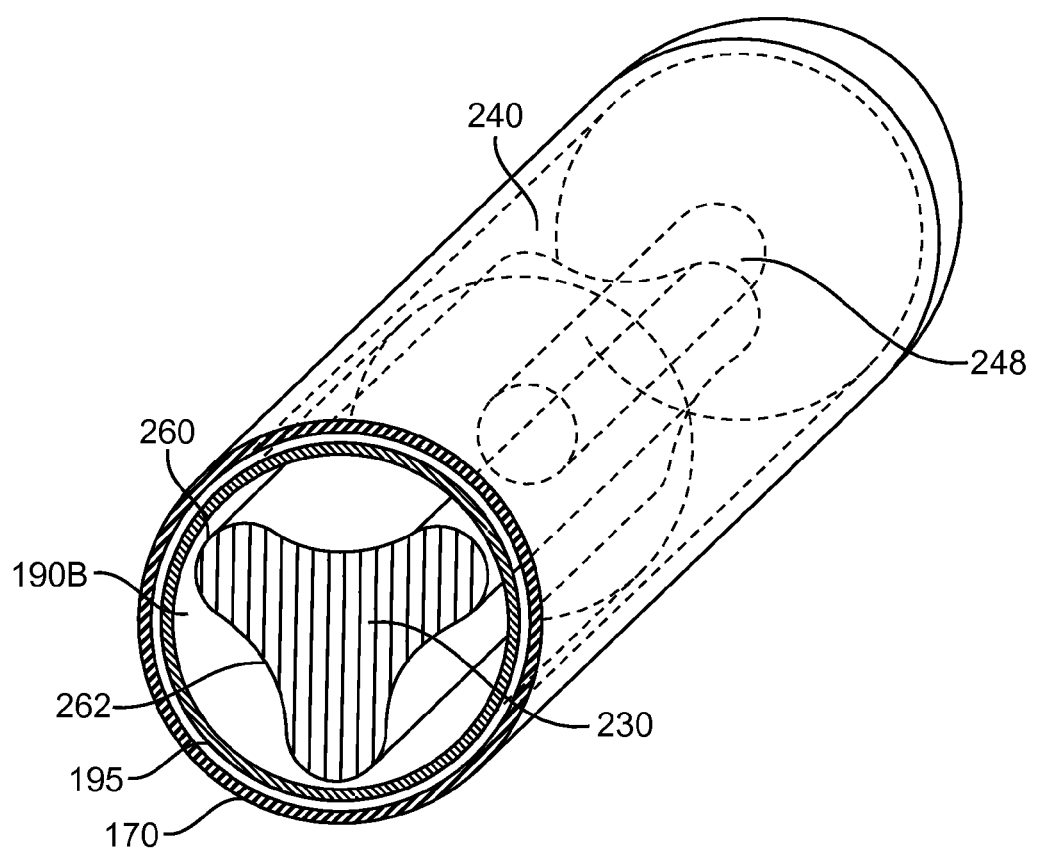
FIG. 13 is an enlarged perspective view of a portion of the working end of FIG. 12C showing an interior chamber and a fluted projecting element.

FIG. 13 shows the cross-section of the ceramic projecting element 230 which may be fluted, and which in one embodiment has three flute elements 260 and three corresponding axial grooves 262 in its surface. Any number of flutes, channels or the like is possible, for example from two to about 20. The fluted design increases the available cross-sectional area at the proximal end of the projecting element 230 to push the tissue strip 225, while at the same time the three grooves 262 permit the proximally-directed jetting of water vapor to impact the tissue exposed to the grooves 262. In one embodiment, the axial length D (FIG. 12A) of the projecting element 230 is configured to push tissue entirely out of the reduced cross-sectional region 190B of the electrode sleeve element 195. In another embodiment, the volume of the chamber 240 is configured to capture liquid that when explosively vaporized provides a gas (water vapor) volume sufficient to expand into and occupy at least the volume defined by a 10% of the total length of extraction channel 160 in the device, usually at least 20% of the extraction channel 160, often at least 40% of the extraction channel 160, sometimes at least 60% of the extraction channel 160, other times at least 80% of the extraction channel 160, and sometimes at least 100% of the extraction channel 160.

As can be understood from FIGS. 12A to 12C, the distending fluid 244 in the working space replenishes the captured fluid in chamber 240 as the cutting sleeve 175 moves in the proximal direction or towards its non-extended position. Thus, when the cutting sleeve 175 again moves in the distal direction to cut tissue, the interior chamber 240 is filled with fluid 244 which is then again contained and is then available for explosive vaporization as described above when the cutting sleeve 175 closes the tissue-receiving window 176. In another embodiment, a one-way valve can be provided in the distal tip 232 to draw fluid directly into interior chamber 240 without the need for fluid to migrate through window 176.

Figure 15:
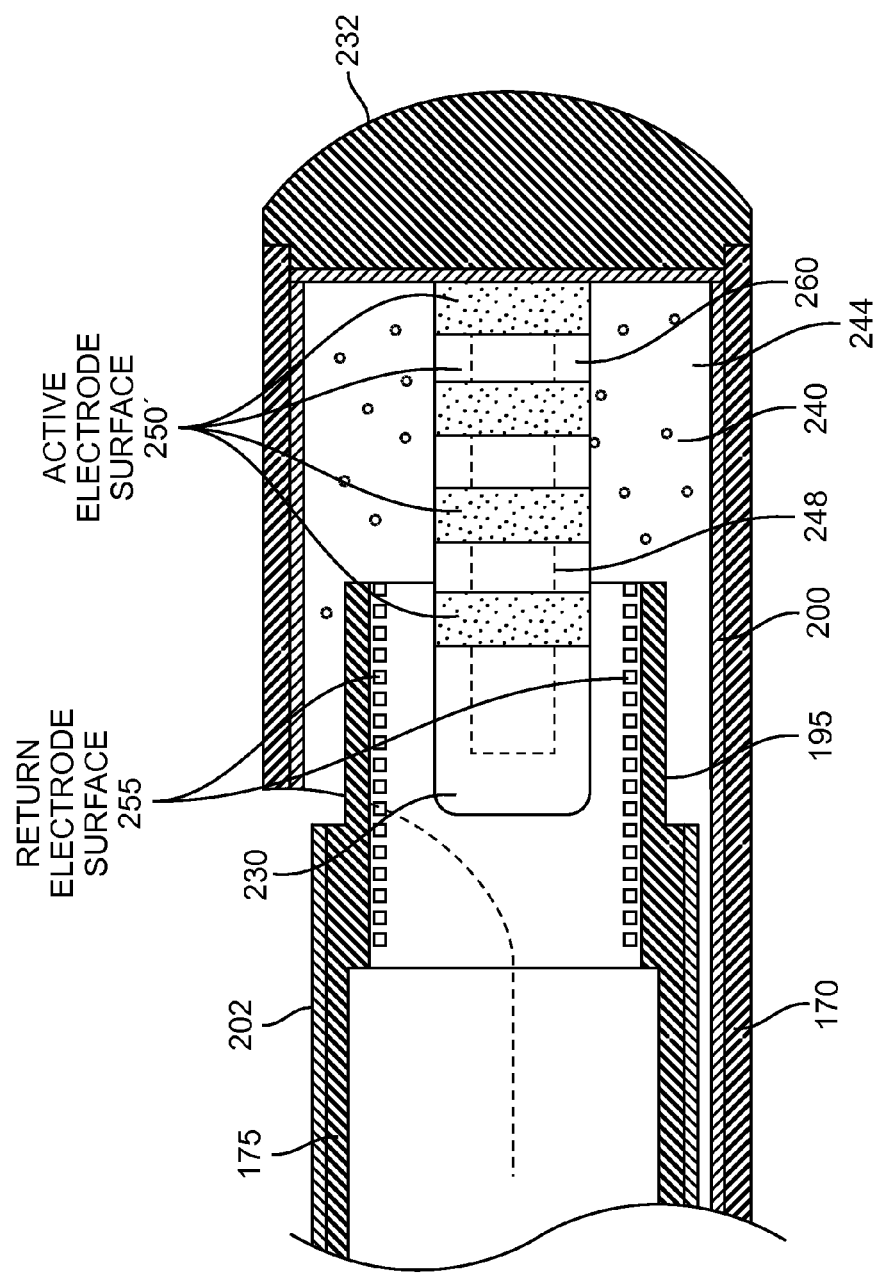
FIG. 15 is a sectional view of the working end of FIG. 12C showing an interior chamber and a variation of a projecting element configured to explosively vaporize the captured liquid volume.

FIG. 15 illustrates another variation in which the active electrode surface area 250' in the second mode comprises a projecting element 230 with conductive regions and non-conductive regions 260 which can have the effect of distributing the focused RF energy delivery over a plurality of discrete regions each in contact with the captured fluid 244. This configuration can more efficiently vaporize the captured fluid volume in chamber 240. In one embodiment, the conductive regions 250' can comprise metal discs or washers on post 248. In other variation (not shown) the conductive regions 250' can comprise holes, ports or pores in a ceramic material 260 fixed over an electrically conductive post 248.

In another embodiment, the RF source 150 and controller 155 can be programmed to modulate energy delivery parameters during stroke X and stroke Y in FIGS. 12A-12C to provide the optimal energy (i) for plasma cutting with electrode edge 180, and (ii) for explosively vaporizing the captured fluid in chamber 240.

Figure 16A:
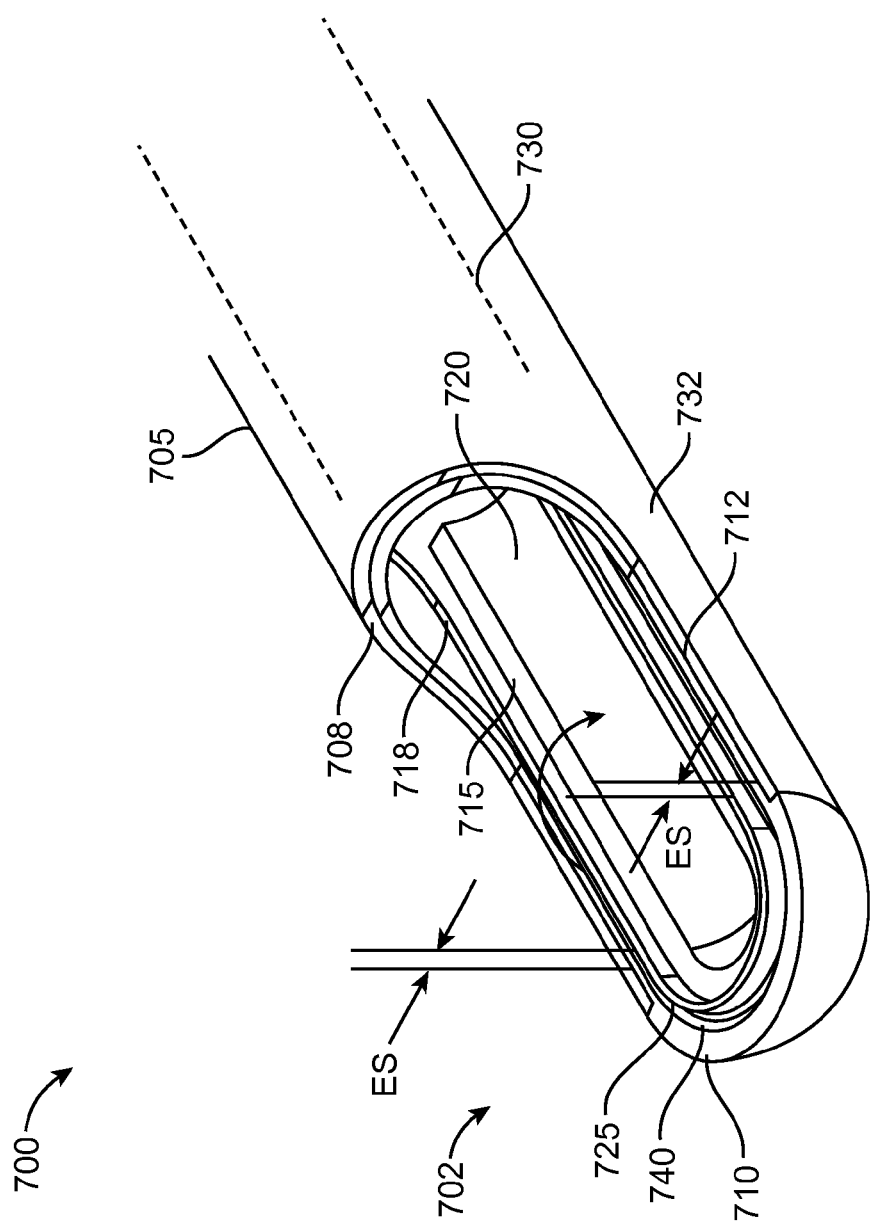
FIG. 16A is a perspective view of an alternative working end with a rotational cutter in a window open position.
Figure 16B:
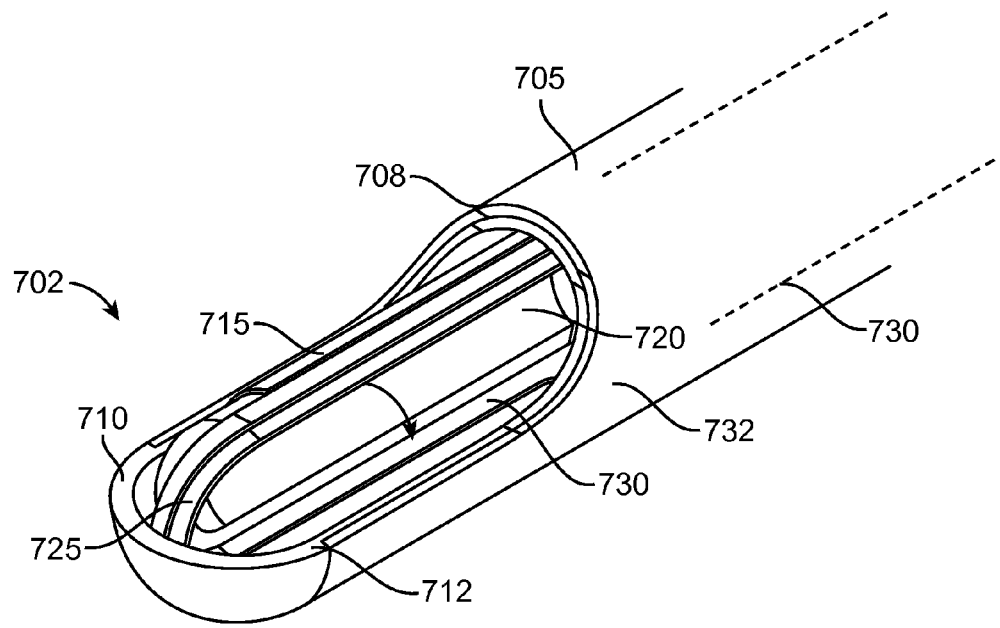
FIG. 16B is a perspective view of the working end of FIG. 16A with the rotating cutting element in a second position.
Figure 16C:
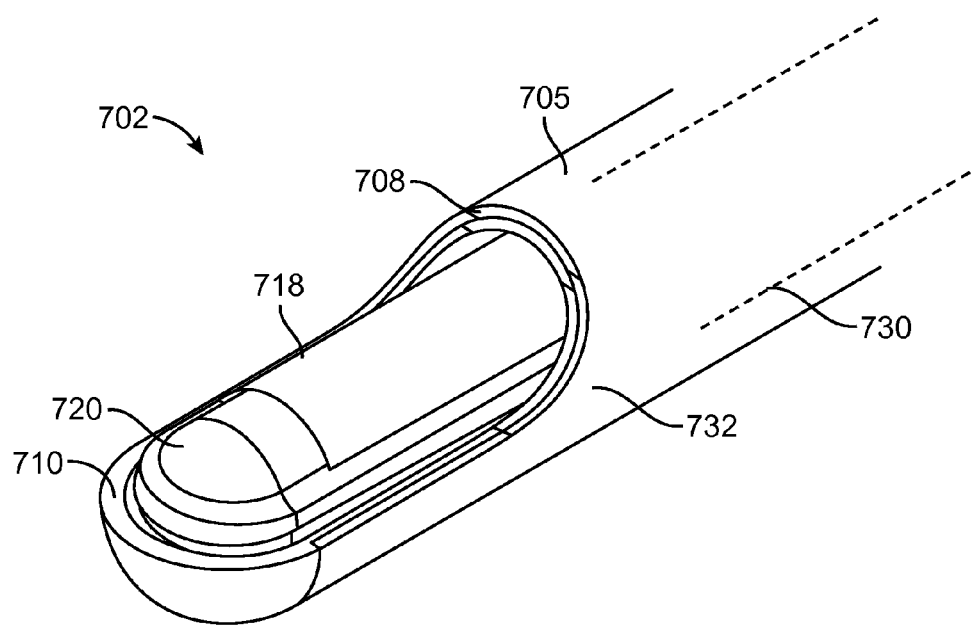
FIG. 16C is a view of the working end of FIGS. 16A-16B with the rotating cutting element in a third position.

FIGS. 16A-16C illustrate another embodiment RF cutting probe 700 with working end 702 comprising a tubular cutter adapted for electrosurgical cutting and extracting targeted tissue from the interior of a patient's body. However, in this embodiment, the inner cutting sleeve is configured to rotate instead of reciprocate as in the previously-described embodiments.

Referring to FIG. 16A, the outer sleeve 705 comprises a metal tubular member 708 that extends from a handle (not shown) to a working end 702 that again carries a distal dielectric body 710 defining a window 712 therein. The inner second sleeve or cutting sleeve 715 comprises a metal tubular member 718 that carries a distal dielectric body 720 with a windowed side 724 that is adapted to cooperate with window 712 in the outer sleeve 705.

FIGS. 16B-16C show the working end 702 of probe 700 with the rotating cutting sleeve 715 and RF electrode edge 725 in two different rotational positions with respect to outer sleeve 705 and window 712. In FIG. 16B, the inner sleeve 715 is rotated approximately 90° relative to the outer sleeve 705. In FIG. 16C, the inner sleeve 715 is rotated 180° to a position relative to inner sleeve 715 to effectively close the window 712 defined by the outer sleeve 705. It can easily be understood how rotation of electrode edge 725 thus can cut tissue during rotation and capture the tissue in the window-closed position within the tissue-receiving lumen 730 of the probe.

In this embodiment of FIGS. 16A-16C, the RF electrode edge 725 of the inner sleeve 715 comprises a first polarity electrode. The exterior surface 732 of the outer sleeve 705 comprises a second polarity electrode as described in previous embodiments. As can be understood from FIGS. 16A-16C, it is critical that the first and second polarity electrode surfaces (725 and 732) are spaced apart by a predetermined dimension throughout the rotation of inner sleeve 715 relative to outer sleeve 705. In one aspect the invention, the distal ends of the inner and outer sleeves comprise ceramic bodies 710 and 720 with an interface 740 therebetween. In other words, the ceramic bodies 710 and 720 rotate about interface 740 and the bodies provide exact electrode spacing ES between the first and second polarity electrodes 725 and 732.

Figure 17:
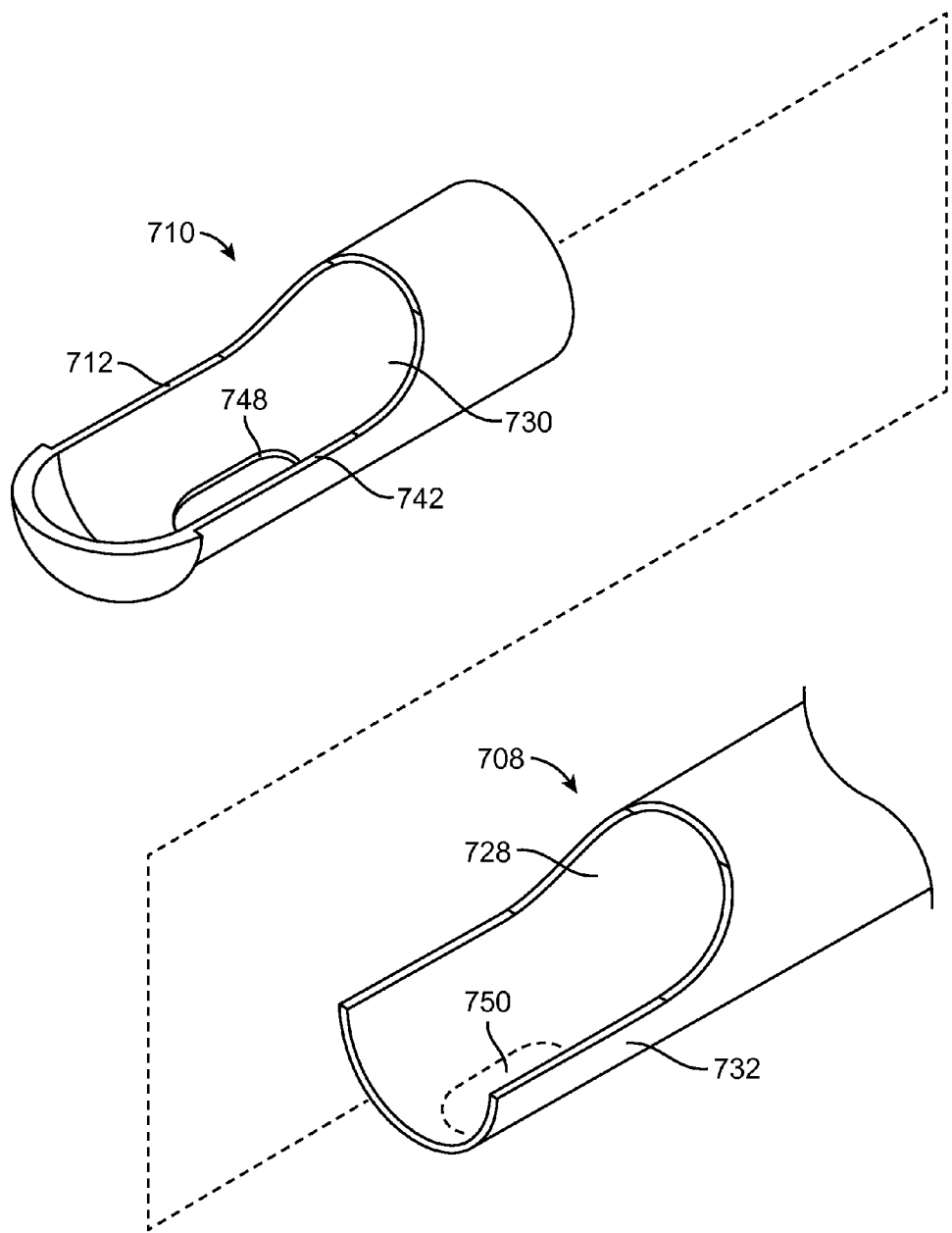
FIG. 17 is an exploded view of the outer sleeve of the working end of FIGS. 16A-16C showing the mating components comprising a ceramic body and a metal tube.

Now referring to FIG. 17, it can be seen how the outer sleeve 705 comprises as an assembly between the tubular metal sleeve 708 and the dielectric body 710, which in this variation can be a ceramic such as zirconium. In FIG. 17, it can be seen that the ceramic body 710 has a thin wall 742 which can range in thickness from about 0.003" and 0.010" wherein the ceramic extends 360° around window 712. Ceramic body 710 can thus be slidably inserted into and bonded to bore 728 in metal sleeve 708.

Figure 18:
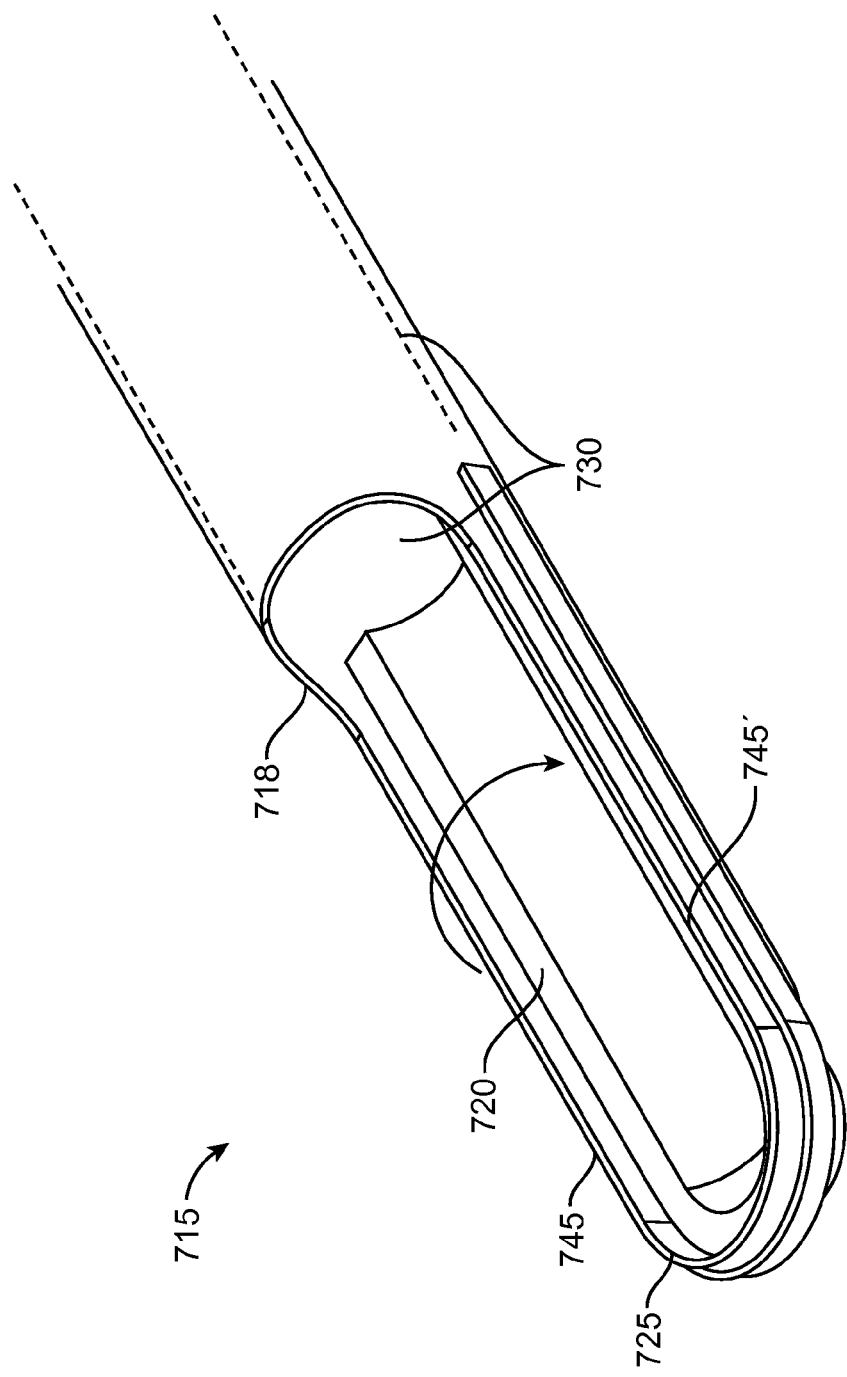
FIG. 18 is a view of the inner sleeve of the working end of FIGS. 16A-16C de-mated from the outer sleeve.
Figure 19:
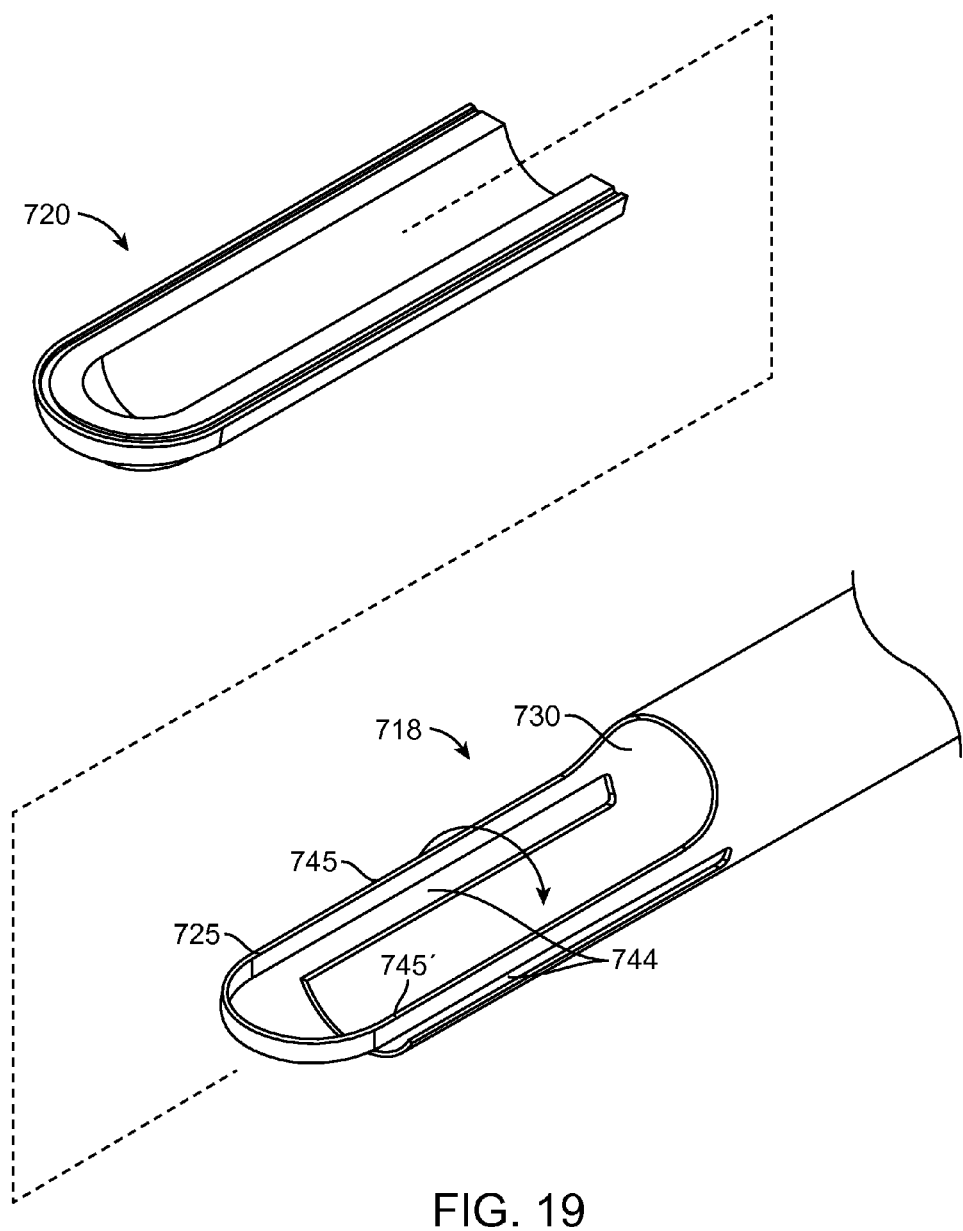
FIG. 19 is an exploded view of the inner sleeve of FIG. 18 showing the mating components comprising a ceramic body and a metal tube.

Now turning to FIG. 18, the distal end of inner sleeve 715 is shown de-mated from the outer sleeve assembly 705 (see FIG. 16A). The tubular metal sleeve 718 of FIG. 18 is fabricated to allow insertion of the ceramic body 720 which supports the electrode edge 725 and provides a rotational bearing surface about the interface 740 (see FIG. 16A). FIG. 19 shows an exploded view of the inner sleeve assembly of FIG. 18. In FIG. 19, it can be seen that ceramic body 720 has a hemispherical cross-sectional shape and includes an elongated slots 744 for receiving and supporting an electrode edge 725. FIG. 19 further shows metal sleeve 718 without ceramic body 720 wherein the electrode edge 725 is cut from a rounded end sleeve 718. It can be understood that the slot 744 can receive ceramic body 720 and thus the electrode edge 725 extends in a loop and under rotation will have a leading edge 745 and a trailing edge 745' depending on the direction of rotation. As used herein, the term 'leading edge' refers to the electrode edge 725 extending around the distal end of the sleeve 715 to its centerline on its rotational axis.

In one aspect of the invention, the tissue cutting probe 700 comprises an outer sleeve 705 and an inner sleeve 715 that is rotatable to provide window-open and window-closed positions and wherein the distal ends of the first and second sleeves 705, 715 include ceramic bodies 710, 720 that provide surfaces on either side of a rotational interface 740. Further, the first and second sleeves provide ceramic bodies 710, 720 that contact one another on either side of the rotational interface 740 and thus provide a predetermined electrode spacing ES (FIG. 16A). In one variation, the wall thickness of the ceramic body 710 is from 0.003" to 0.004". Likewise, the wall thickness of ceramic body 720 can be from 0.003" to 0.004". Thus, the radial dimension between the first and second polarity electrodes at a minimum in this variation is 0.006". In another variation in which the inner sleeve 715 carries an outer polymeric dielectric layer which can be 0.001" in thickness to thus provide an electrode spacing dimension ES of 0.004". In other variations having a larger diameter, the dimension between the first and second polarity electrodes can range up to 0.030". In general, the scope of the invention includes providing a rotational tubular cutter with bi-polar electrodes spaced apart between 0.004" inches and 0.030" inches wherein the cutting sleeve 715 rotates about an interface 740 having dielectric materials on either side thereof.

In the embodiment shown in FIGS. 16A-16C, the length of the window can range from about 5 mm to 30 mm. The diameter of the probe working end can range from about 3 mm to 6 mm or more. The rotational speed of the inner sleeve can range from 100 rpm to 5,000 rpm. In one embodiment, a rotation ranging from about 200 rpm to 500 rpm cut tissue efficiently and allowed for effective tissue extraction as described below.

Figure 20A:
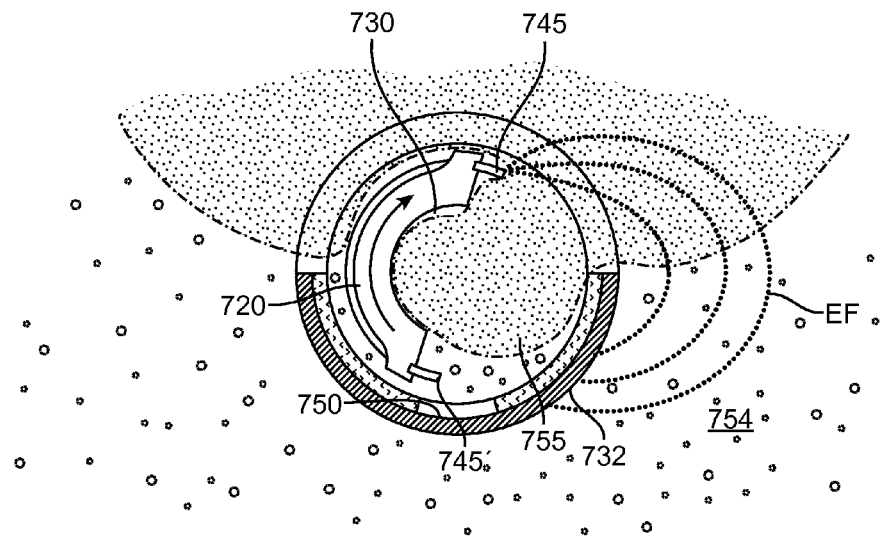
FIG. 20A is a cross sectional view of the working end of FIGS. 16A-16C with the rotating inner sleeve in a first position cutting tissue in a first RF mode.
Figure 20B:
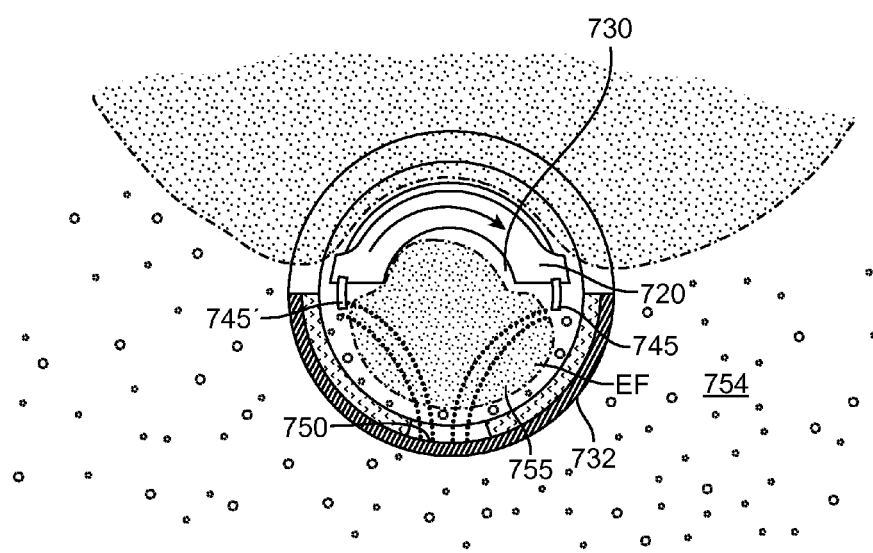
FIG. 20B is a cross sectional view of the working end of FIG. 20A with the rotating inner sleeve in a second window-closed position with a second RF mode vaporizing saline captured in the interior extraction channel.

In another aspect of the invention, referring to FIGS. 17, 20A and 20B, it can be seen that an opening 748 is provided in ceramic body 710 which provides exposure through the ceramic body 710 to metal sleeve 708 which comprises the first polarity electrode when assembled. Thus, the metal sleeve provides an interior electrode surface 750 that is exposed to interior chamber 730. It can be understood that in this variation, the working end 702 can function in two RF modes as described in the previous reciprocating probe embodiments (see FIGS. 12A-12C). In the first RF mode, the exterior surface 732 of outer sleeve 705 functions as a first polarity electrode in the interval when the inner sleeve 715 and its second polarity electrode edge 725 rotates from the window-open position of FIG. 16A toward the window-closed position of FIG. 16B. FIG. 20A depicts this interval of rotation, wherein it can be seen that the first RF mode operates for approximately 180° of rotation of the inner cutting sleeve 715. In this position depicted in FIG. 20A, the leading edge 745 and trailing edge 745' of electrode edge 725 are exposed to the open window 712 and electric fields EF extend to the first polarity electrode surface 732 about the exterior of the probe and plasma is formed at leading edge 745 to cut tissue.

The second RF mode is shown in FIG. 20B, wherein the inner sleeve 715 rotates to the window-closed position and the probe switches instantly to such a second RF mode since the electrode edge 725 is exposed only to the tissue-receiving lumen 730. It can be understood that the second RF mode operates only when the window 712 is closed as in FIGS. 16C and 20B which causes the instant explosive vaporization of captured saline in the lumen 730. In FIG. 20B, it can be seen that the electrode edge 725 is exposed only to the interior of lumen 730 and electric fields EF extend between the leading and trailing electrode edges (745 and 745') to the exposed electrode surface 750 to thus cause the explosive vaporization of captured saline. The vaporization occurs instantly within limited degrees of rotation of the inner sleeve, e.g., 5° to 20° of rotation, upon closing the window 712 to thereby expel the resected tissue in the proximal direction as described previously. It has been found that saline captured in the interior channel 730 can be distal to the resected tissue or adjacent to the resected tissue in the lumen and the fluid expansion in the liquid-to-vapor transition will instantly expel the resected tissue outwardly or proximally in lumen 730.

Figure 21:
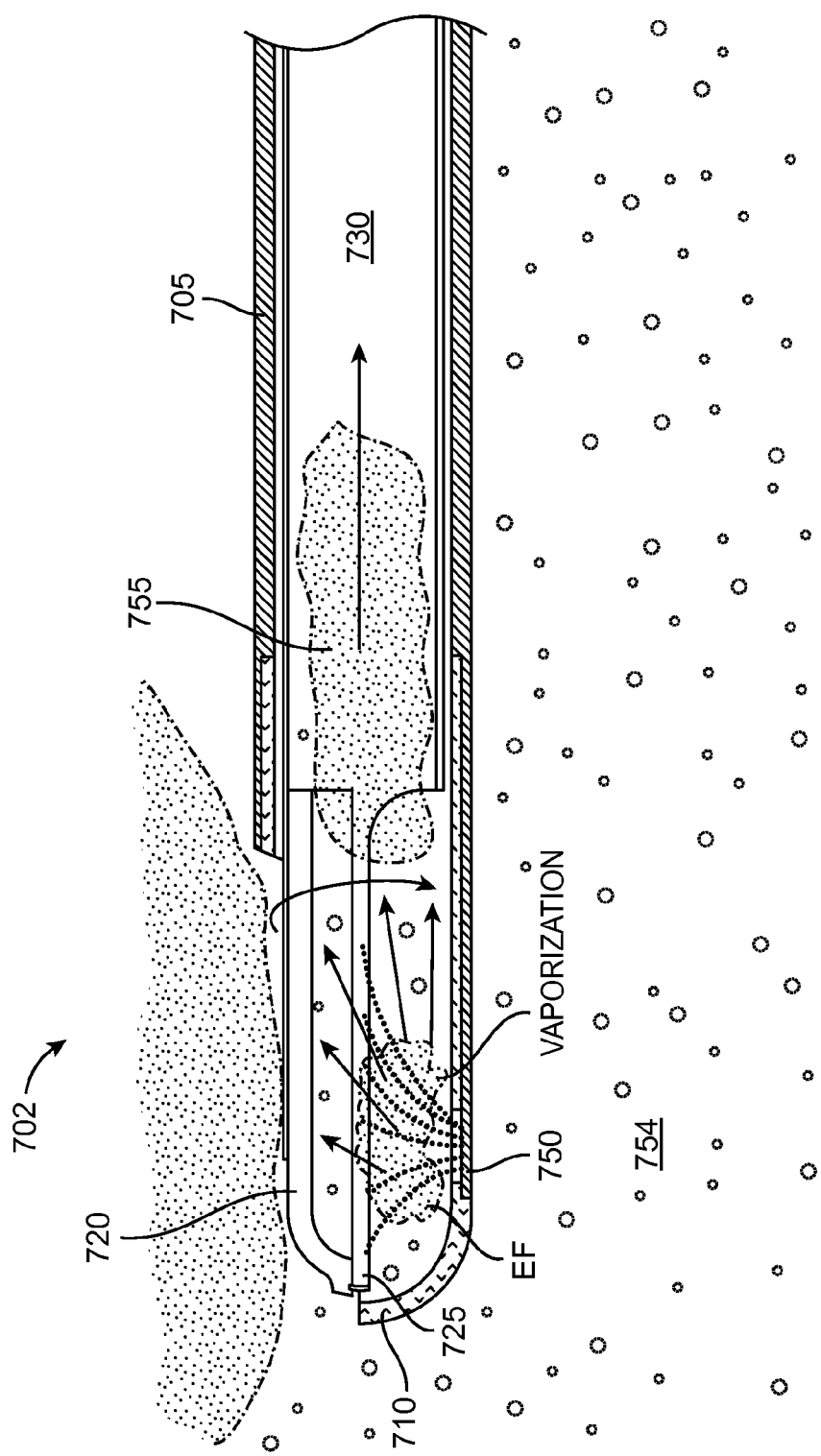
FIG. 21 is a longitudinal sectional view corresponding to the view of FIG. 20B with the rotating inner sleeve in a window-closed position and with the second RF mode vaporizing saline captured in the interior extraction channel to expel tissue proximally.

FIG. 21 is a longitudinal sectional view of the working end 702 corresponding to FIG. 20B wherein the electrical fields EF are confined within the interior lumen 730 to thus cause the explosive vaporization of captured saline. Thus, the second RF mode and the vaporization of captured saline 754 as depicted in FIG. 20B will expel the resected tissue 755 proximally within the tissue extraction channel 730 that extends proximally through the probe to a collection reservoir as described in previous embodiments. In general, a method of the invention includes capturing a tissue volume in a closed distal portion of an interior passageway of an elongate probe and causing a phase transition in a fluid proximate to the captured tissue volume to expand the fluid to apply a proximally directed expelling force to the tissue volume. The time interval for providing a closed window to capture the tissue and for causing the explosive vaporization can range from about 0.01 second to 2 seconds. A negative pressure source also can be coupled to the proximal end of the extraction lumen as described previously.

Figure 22:
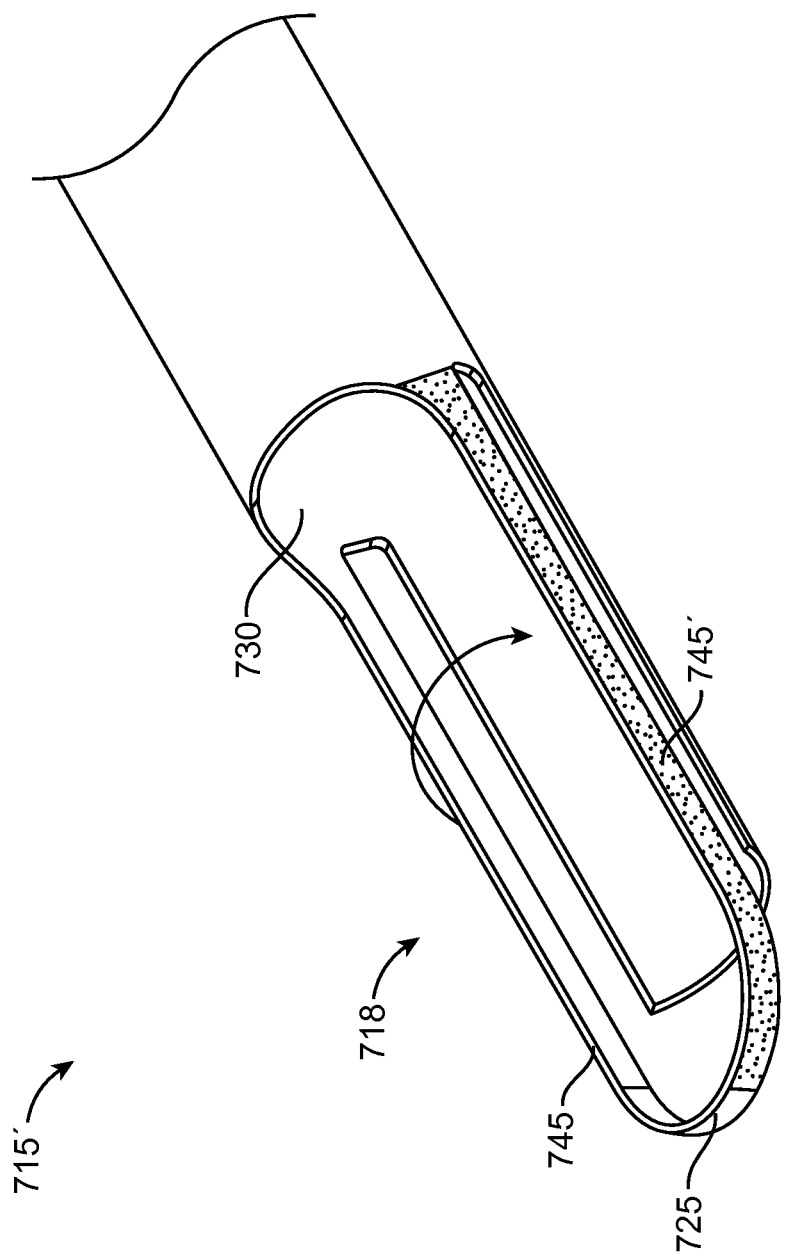
FIG. 22 is a view of an alternative embodiment of a metal tube component of an inner sleeve.

Now turning to FIG. 22, another variation of inner sleeve 715' is shown. In this embodiment, the leading edge 745 and the trailing edge 745' of electrode edge 725 are provided with different electrical characteristics. In one variation, the leading edge 745 is a highly conductive material suited for plasma ignition as described previously. In this same variation shown in FIG. 22, the trailing edge 745' comprises a different material which is less suited for plasma formation, or entirely not suited for plasma formation. In one example, the trailing edge 745' comprises a resistive material (e.g., a resistive surface coating) wherein RF current ignites plasma about the leading edge 745 but only resistively heats the trailing 745' edge to thus provide enhanced coagulation functionality. Thus, the leading edge 745 cuts and the trailing edge 745' is adapted to coagulate the just-cut tissue. In another variation, the trailing edge 745' can be configured with a capacitive coating which again can be used for enhancing tissue coagulation. In yet another embodiment, the trailing edge 745' can comprise a positive temperature coefficient of resistance (PTCR) material for coagulation functionality and further for preventing tissue sticking. In another variation, the trailing edge 745' can have a dielectric coating that prevents heating altogether so that the leading edge 745 cut tissues and the trailing edge 745' has no electrosurgical functionality.

Figure 23:
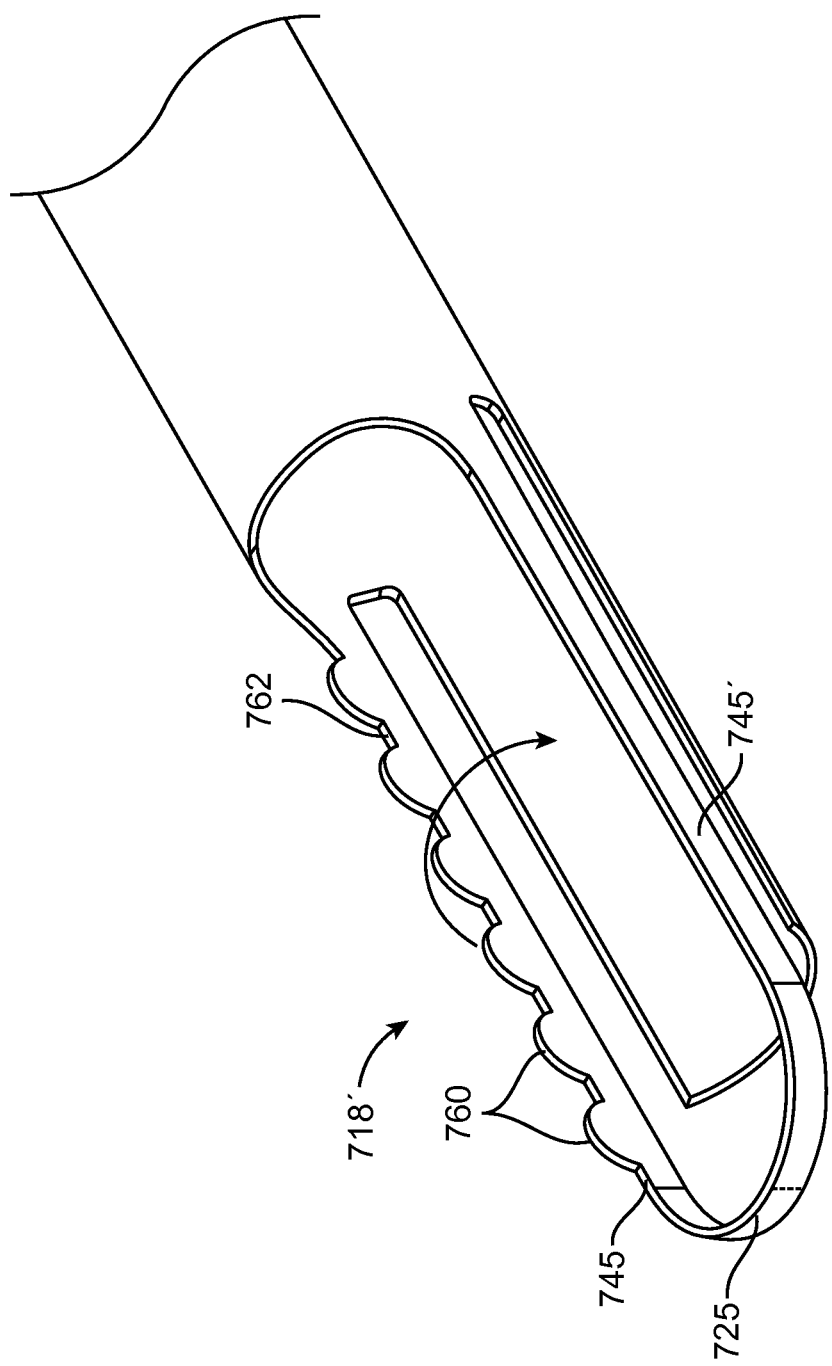
FIG. 23 is a view of an alternative embodiment of a metal tube component of an inner sleeve.

FIG. 23 illustrates another embodiment of inner sleeve component 718' in which the electrode edge 725 has a leading edge 745 with edge features for causing a variable plasma effect. In this embodiment, the projecting edges 760 of the leading edge 745 electrode will create higher energy density plasma than the scalloped or recessed portions 762 which can result in more efficient tissue cutting. In another embodiment, the electrode surface area of the leading edge 745 and trailing edge 745' can differ, again for optimizing the leading edge 745 for plasma cutting and the trailing edge 745' for coagulation. In another embodiment, the trailing edge 745' can be configured for volumetric removal of tissue by plasma abrasion of the just-cut surface since it wiped across the tissue surface. It has been found that a substantial amount of tissue (by weight) can be removed by this method wherein the tissue is disintegrated and vaporized. In general, the leading edge 745 and trailing edge 745' can be dissimilar with each edge optimized for a different effect on tissue.

Figure 24:
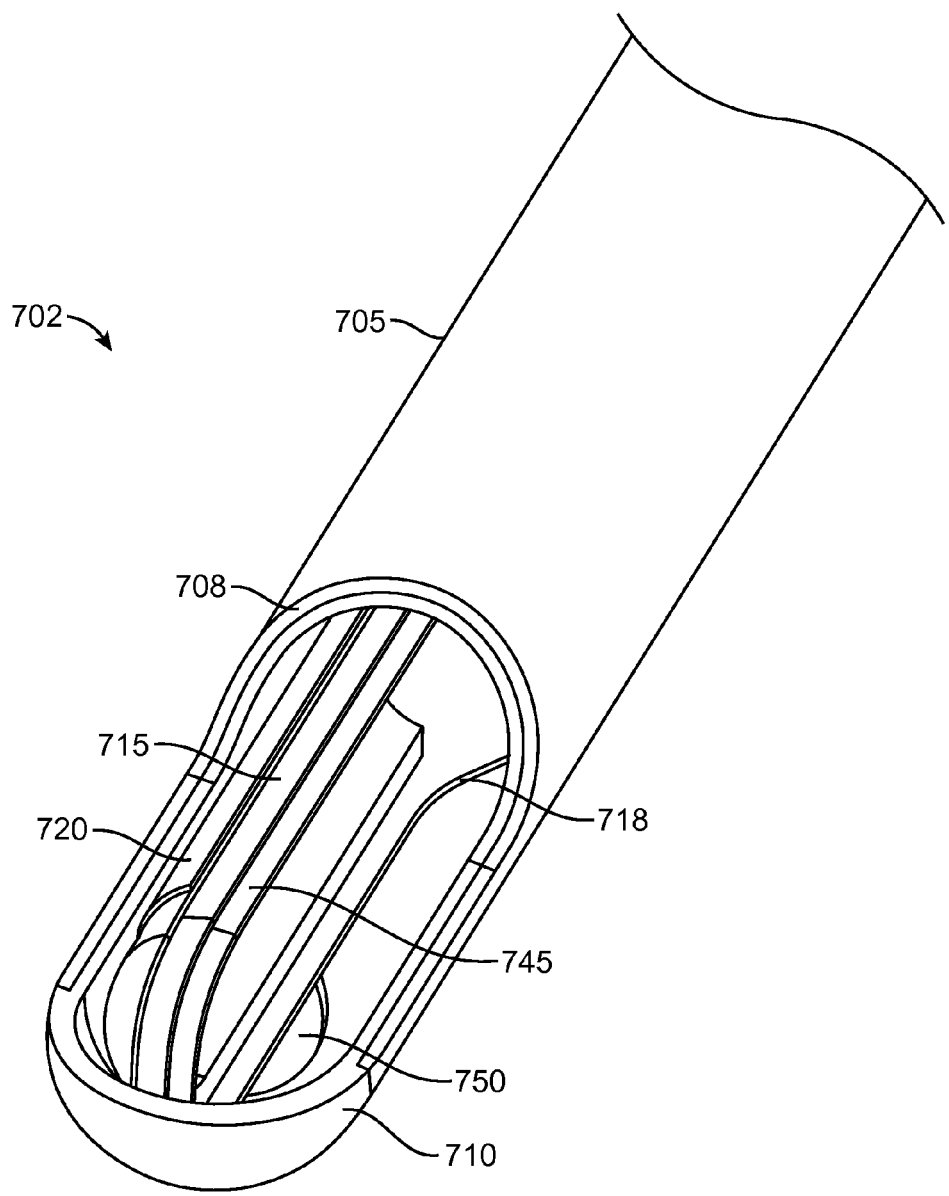
FIG. 24 is a perspective view of an alternative probe that is configured to stop the inner rotating sleeve in a particular position.

FIG. 24 illustrates another aspect of the invention that can be adapted for selective cutting or coagulating of targeted tissue. In this variation, a rotation control mechanism is provided to which can move the inner sleeve 715 to provide the leading edge 745 in an exposed position and further lock the leading edge 745 in such an exposed position. In this locked (non-rotating) position, the physician can activate the RF source and controller to ignite plasma along the exposed leading edge 745 and thereafter the physician can use the working end as a plasma knife to cut tissue. In another variation, the physician can activate the RF source and controller to provide different RF parameters configured to coagulate tissue rather than to cut tissue. In one embodiment, a hand switch or foot switch can upon actuation move and lock the inner sleeve in the position shown in FIG. 24 and thereafter actuate the RF source to deliver energy to tissue.

It should be appreciated that while an RF source is suitable for causing explosive vaporization of the captured fluid volume, any other energy source can be used and falls within the scope of the invention, such as an ultrasound tranducer, HIFU, a laser or light energy source, a microwave or a resistive heat source.

In another embodiment, the probe can be configured with a lumen in communication with a remote liquid source to deliver fluid to the interior chamber 240.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. An electrosurgical system for resecting and extracting tissue, said system comprising:
    an elongated probe including an inner sleeve which includes a first polarity electrode and defines a tissue extraction lumen therein, and an outer sleeve which includes a second polarity electrode;
    wherein the first polarity electrode is disposed at a distal end of the inner sleeve and is movable therewith, wherein movement of the first polarity electrode is dependent upon movement of the inner sleeve;
    wherein the inner sleeve reciprocates within the outer sleeve, and wherein the elongate probe is configured to operate in a first mode wherein the inner sleeve is advanced to resect and capture tissue and in a second mode wherein a fluid volume within the outer sleeve is vaporized by application of RF energy between the first and second polarity electrodes in order to expel tissue captured by operating in the first mode.

2. The system of claim 1 wherein the first mode is a RF resecting mode.

3. The system of claim 1 wherein the fluid volume vaporized expands and is configured to expel captured tissue proximally through the tissue extraction lumen.

4. The system of claim 3 wherein the fluid volume is in a distal-most region of the tissue extraction lumen and the electrodes are configured to explosively vaporize the fluid volume to expel captured tissue proximally in the tissue extraction lumen.

5. The system of claim 1 further comprising a negative pressure source operatively coupled to the tissue extraction lumen therein.

6. The system of claim 1 further comprising a radiofrequency generator configured to provide the same RF parameters for both the first and second modes.

7. The system of claim 1 further comprising a radiofrequency generator configured to provide different RF parameters for the first and second modes.

8. The system of claim 1 further comprising a controller which provides a range of reciprocation rates for the inner sleeve.

9. The system of claim 8 wherein the reciprocation rate range is from 0.5 Hz to 10 Hz.

10. A medical system for extracting tissue from the interior of a patient's body, comprising:
    an elongated probe comprising an outer sleeve and an inner sleeve with a tissue extraction lumen therein;
    wherein the outer sleeve at least partially defines a chamber configured to receive a selected liquid volume in an open configuration, said chamber being in communication with a distal end of the tissue extraction lumen;
    wherein the inner sleeve includes a first polarity electrode disposed thereon configured to electrosurgically resect tissue disposed within the chamber upon advancement of the inner sleeve relative thereto; and
    means for delivering energy to the chamber when the chamber is in a closed configuration, thereby vaporizing liquid within the chamber such that a resulting vapor occupies a volume defined by at least 10% of the total length of the extraction lumen;
    wherein movement of the inner sleeve relative to the outer sleeve shifts the chamber between the open configuration and the closed configuration.

11. The medical system of claim 10 wherein the resulting vapor occupies a volume defined by at least 20% of the total length of the extraction lumen.

12. The medical system of claim 10 wherein the resulting vapor occupies a volume defined by at least 40% of the total length of the extraction lumen.

13. The medical system of claim 10 wherein the resulting vapor occupies a volume defined by at least 60% of the total length of the extraction lumen.

14. The medical system of claim 10 wherein the resulting vapor occupies a volume defined by at least 80% of the total length of the extraction lumen.

15. The medical system of claim 10 wherein the resulting vapor occupies a volume defined by the entire length of the extraction lumen.

16. A medical system for resecting and extracting tissue, said system comprising:
   an elongated probe including:
      an inner sleeve defining a tissue extraction lumen therein; and
      an outer sleeve defining a chamber having a closed distal end and a side-opening window;
      wherein the inner sleeve is movable within the outer sleeve to resect and capture tissue extending into the chamber through the window; and
      means for vaporizing liquid within the chamber when the window is closed to expel captured tissue proximally through the tissue extraction lumen.

17. The medical system of claim 16, wherein a distal end of the inner sleeve is disposed adjacent the closed distal end of the outer sleeve when the window is closed.

18. The medical system of claim 16, further including an RF generator operatively coupled to the means for vaporizing liquid.

19. The medical system of claim 18, wherein in a first electrosurgical mode, RF energy density is focused about a distal end of the inner sleeve, and in a second electrosurgical mode, RF energy density is focused within the chamber about the closed distal end of the outer sleeve.

20. The medical system of claim 19, wherein in the first electrosurgical mode, plasma formed at the distal end of the inner sleeve resects tissue extending into the chamber through the window.

* * * * *